United States Patent
Heimbecher et al.

(10) Patent No.: US 10,595,937 B2
(45) Date of Patent: Mar. 24, 2020

(54) SYSTEM FOR OPTIMIZED COUPLING OF ABLATION CATHETERS TO BODY TISSUES AND EVALUATION OF LESIONS FORMED BY THE CATHETERS

(71) Applicant: St. Jude Medical, Atrial Fibrillation Division, Inc., St. Paul, MN (US)

(72) Inventors: Reed R. Heimbecher, Hamel, MN (US); Saurav Paul, Minneapolis, MN (US); Prathyusha Marri, Blaine, MN (US); Steven C. Christian, New Brighton, MN (US); William M. Sutton, Minnetonka, MN (US); Paul H. McDowall, Eden Prairie, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 435 days.

(21) Appl. No.: 14/369,645

(22) PCT Filed: Dec. 27, 2012

(86) PCT No.: PCT/US2012/071801
§ 371 (c)(1),
(2) Date: Jun. 27, 2014

(87) PCT Pub. No.: WO2013/101923
PCT Pub. Date: Jul. 4, 2013

(65) Prior Publication Data
US 2014/0364848 A1 Dec. 11, 2014

Related U.S. Application Data

(60) Provisional application No. 61/581,247, filed on Dec. 29, 2011.

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/6852* (2013.01); *A61B 5/6885* (2013.01);
(Continued)

(58) Field of Classification Search
CPC ........ A61B 18/1492; A61B 2018/1465; A61B 2018/1467; A61B 2018/00648;
(Continued)

(56) References Cited

U.S. PATENT DOCUMENTS

| | | | |
|---|---|---|---|
| 5,341,807 A | 8/1994 | Nardella | |
| 5,391,199 A | 2/1995 | Ben-Haim | |

(Continued)

FOREIGN PATENT DOCUMENTS

| | | | |
|---|---|---|---|
| CN | 101416874 A | 4/2009 | |
| JP | H0663059 A | 3/1994 | |

(Continued)

OTHER PUBLICATIONS

Stevenson W.G., Soejima, K. (2005). Recording Techniques for Clinical Electrophysiology. J Cardiovasc Electrophysiol. 16(9):1017-1022. Retrieved from http://www.medscape.com/viewarticle/512810_2 on Jul. 7, 2016.*

*Primary Examiner* — Eun Hwa Kim
(74) *Attorney, Agent, or Firm* — Dykema Gossett PLLC

(57) ABSTRACT

A system for diagnosis or treatment of tissue in a body is provided. The system includes an ablation catheter having a deformable, elongate shaft having proximal and distal ends. The catheter further includes an ablation delivery member disposed proximate the distal end of the shaft and configured to deliver ablation energy to ablate the tissue. In one embodiment, the ablation delivery member comprises an ablation electrode and may also be configured to generate a signal indicative of electrical activity in the tissue. The catheter further includes one or more sensing electrodes (Continued)

disposed proximate the ablation delivery member. The sensing electrodes are configured to generate signals indicative of electrical activity in the tissue. The system further includes an electronic control unit configured to control delivery of ablation energy from the ablation delivery member responsive to one or more of the generated signals indicative of electrical activity in the tissue.

17 Claims, 22 Drawing Sheets

(51) Int. Cl.
*A61B 18/12* (2006.01)
*A61B 18/00* (2006.01)
*A61B 90/00* (2016.01)

(52) U.S. Cl.
CPC ............ *A61B 18/1206* (2013.01); *A61B 2018/00357* (2013.01); *A61B 2018/00577* (2013.01); *A61B 2018/00648* (2013.01); *A61B 2018/00839* (2013.01); *A61B 2018/00875* (2013.01); *A61B 2018/1465* (2013.01); *A61B 2018/1467* (2013.01); *A61B 2090/065* (2016.02)

(58) Field of Classification Search
CPC ........... A61B 2018/00839; A61B 2018/00357; A61B 2018/00875; A61B 2018/00577; A61B 5/6885; A61B 5/6852; A61B 2090/065

See application file for complete search history.

(56) References Cited

U.S. PATENT DOCUMENTS

| | | | |
|---|---|---|---|
| 5,443,489 A | 8/1995 | Ben-Haim | |
| 5,558,091 A | 9/1996 | Acker et al. | |
| 5,951,471 A | 9/1999 | de la Rama et al. | |
| 6,233,476 B1 | 5/2001 | Strommer et al. | |
| 6,241,724 B1 | 6/2001 | Fleischman et al. | |
| 6,391,024 B1 | 5/2002 | Sun et al. | |
| 6,498,944 B1 | 12/2002 | Ben-Haim et al. | |
| 6,690,963 B2 | 2/2004 | Ben-Haim et al. | |
| 6,751,492 B2 | 6/2004 | Ben-Haim | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,289,843 B2 | 10/2007 | Beatty et al. | |
| 7,386,339 B2 | 6/2008 | Strommer et al. | |
| 7,387,630 B2 | 6/2008 | Mest | |
| 7,389,148 B1* | 6/2008 | Morgan | A61N 1/056 |
| | | | 600/372 |
| 7,536,218 B2 | 5/2009 | Govari et al. | |
| 7,848,789 B2 | 12/2010 | Govari et al. | |
| 7,955,326 B2* | 6/2011 | Paul | A61B 18/1492 |
| | | | 606/32 |
| 8,641,663 B2 | 2/2014 | Kirschenman et al. | |
| 8,814,857 B2 | 8/2014 | Christian | |
| 9,788,891 B2 | 10/2017 | Christian et al. | |
| 9,855,094 B2 | 1/2018 | Christian | |
| 2002/0165448 A1 | 11/2002 | Ben-Haim et al. | |
| 2004/0092806 A1 | 5/2004 | Sagon et al. | |
| 2005/0020974 A1* | 1/2005 | Noriega | A61M 25/0054 |
| | | | 604/95.04 |
| 2005/0033135 A1* | 2/2005 | Govari | A61B 5/053 |
| | | | 600/374 |
| 2007/0100332 A1 | 5/2007 | Paul et al. | |
| 2007/0123764 A1 | 5/2007 | Thao | |
| 2008/0015568 A1 | 1/2008 | Paul et al. | |
| 2008/0161796 A1 | 7/2008 | Cao et al. | |
| 2008/0249522 A1 | 10/2008 | Pappone et al. | |
| 2008/0275428 A1 | 11/2008 | Tegg et al. | |
| 2008/0294158 A1 | 11/2008 | Pappone et al. | |
| 2009/0163904 A1 | 6/2009 | Miller et al. | |
| 2009/0247942 A1 | 10/2009 | Kirschenman | |
| 2009/0247944 A1 | 10/2009 | Kirschenman et al. | |
| 2009/0247993 A1 | 10/2009 | Kirschenman et al. | |
| 2009/0248042 A1 | 10/2009 | Kirschenman | |
| 2010/0069921 A1* | 3/2010 | Miller | A61B 18/1233 |
| | | | 606/130 |
| 2010/0152731 A1* | 6/2010 | de la Rama | A61M 25/007 |
| | | | 606/41 |
| 2010/0168735 A1 | 7/2010 | Deno et al. | |
| 2010/0204560 A1 | 8/2010 | Salahieh et al. | |
| 2010/0228247 A1 | 9/2010 | Paul et al. | |
| 2010/0256558 A1 | 10/2010 | Olson et al. | |
| 2010/0298826 A1 | 11/2010 | Leo et al. | |
| 2011/0022045 A1 | 1/2011 | Cao et al. | |
| 2011/0118727 A1 | 5/2011 | Fish et al. | |
| 2011/0125150 A1 | 5/2011 | Deno et al. | |
| 2011/0270046 A1 | 11/2011 | Paul et al. | |
| 2011/0288392 A1 | 11/2011 | de la Rama et al. | |
| 2011/0313417 A1 | 12/2011 | de la Rama et al. | |

FOREIGN PATENT DOCUMENTS

| | | | |
|---|---|---|---|
| JP | | 2002113014 A | 4/2002 |
| JP | | 2005199072 A | 7/2005 |
| JP | | 2009090114 A | 4/2009 |
| JP | | 2009-518130 | 5/2009 |
| JP | | 2009518151 A | 5/2009 |
| JP | | 3161030 U | 7/2010 |
| JP | | 2010259810 A | 11/2010 |
| JP | | 2011508628 A | 3/2011 |
| JP | | 2011131061 A | 7/2011 |
| JP | | 2011183165 A | 9/2011 |
| WO | | 2004100813 | 11/2004 |
| WO | WO | 2009/120982 | 10/2009 |
| WO | | 2010/056771 A1 | 5/2010 |
| WO | | 2010/078453 A1 | 7/2010 |
| WO | | 2011/062681 A1 | 5/2011 |
| WO | | 2011/159861 A2 | 12/2011 |
| WO | | 2011/159955 A1 | 12/2011 |

* cited by examiner

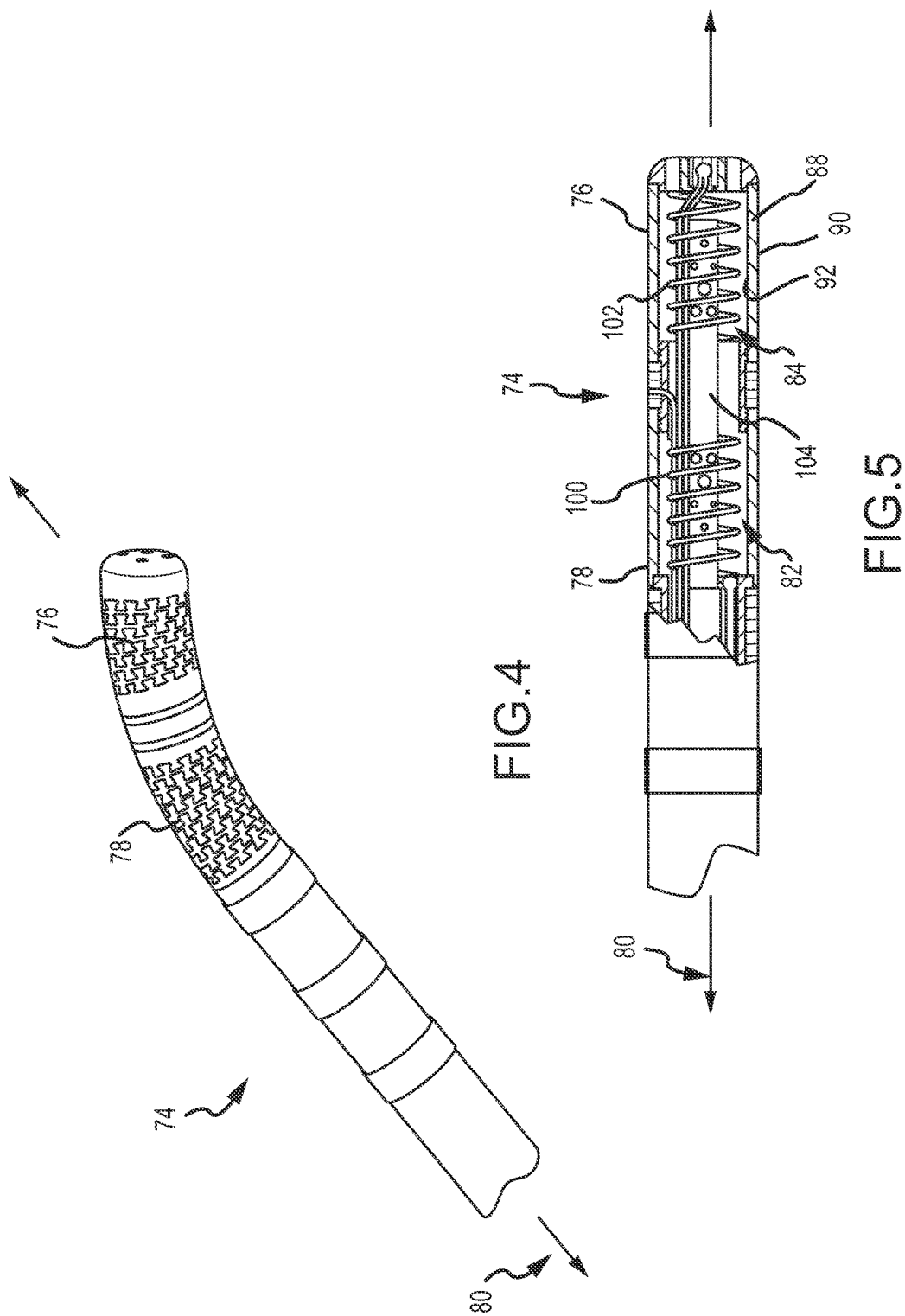

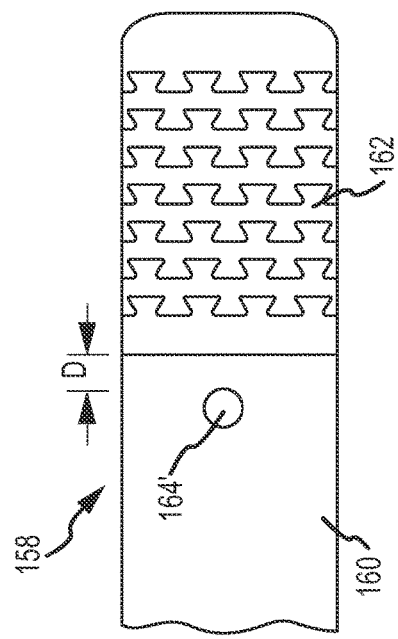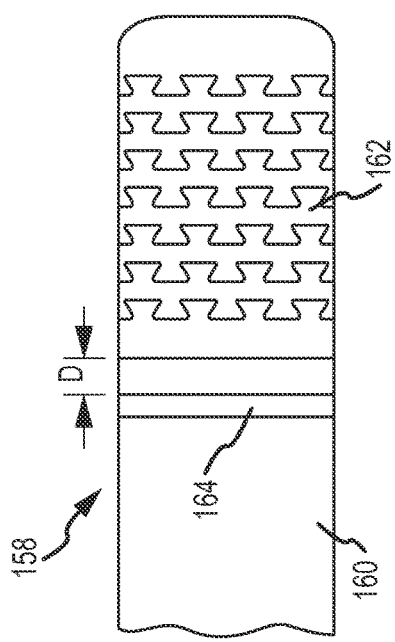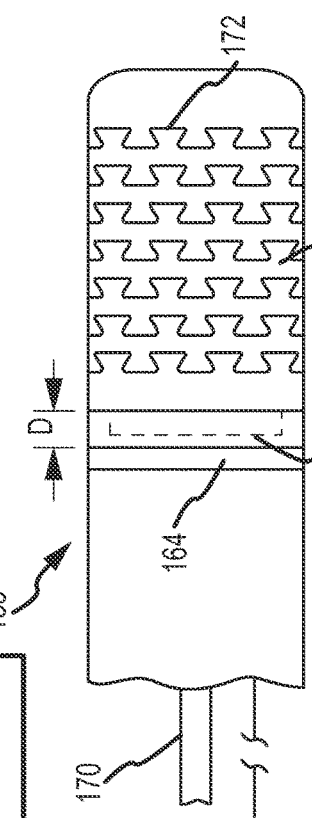

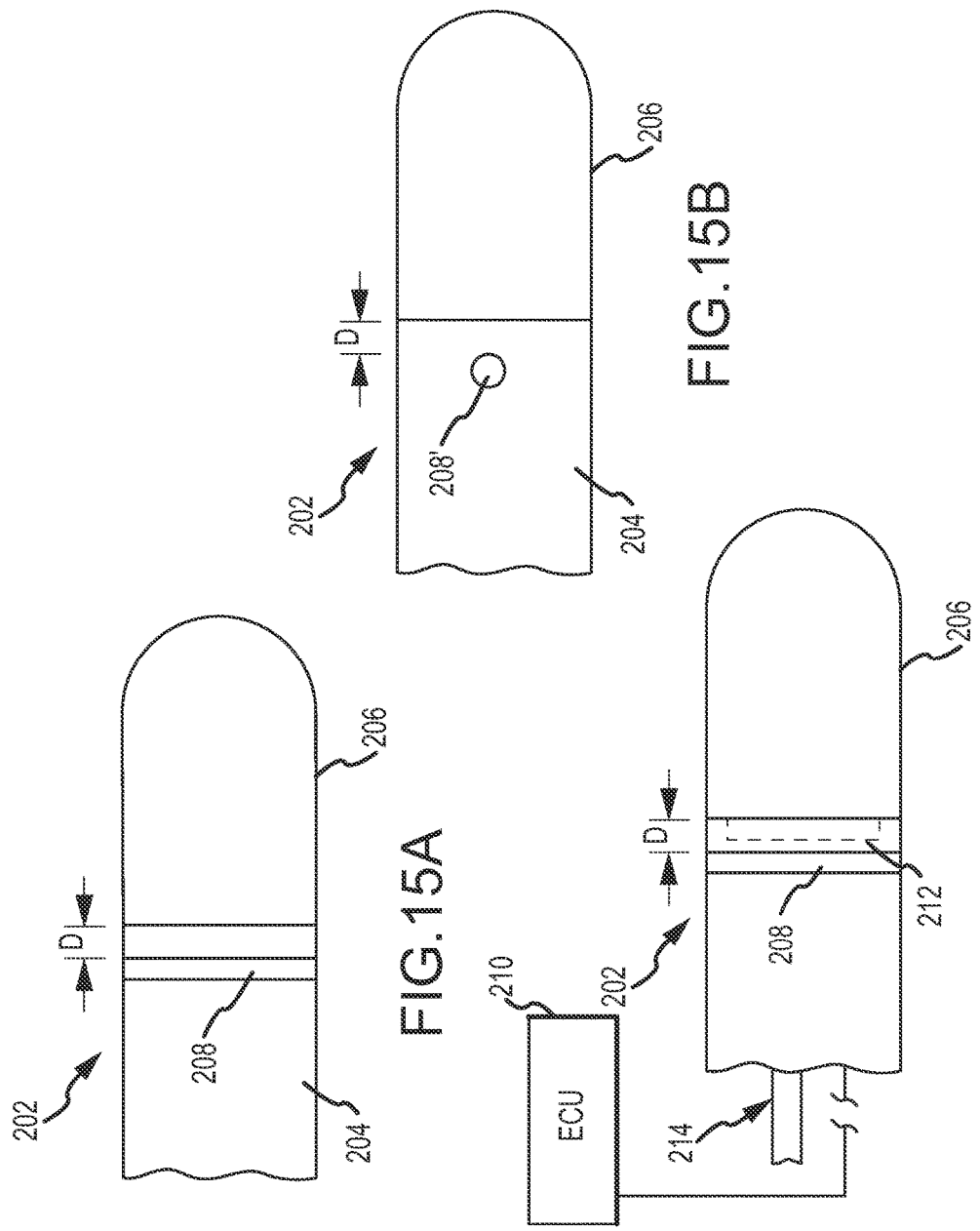

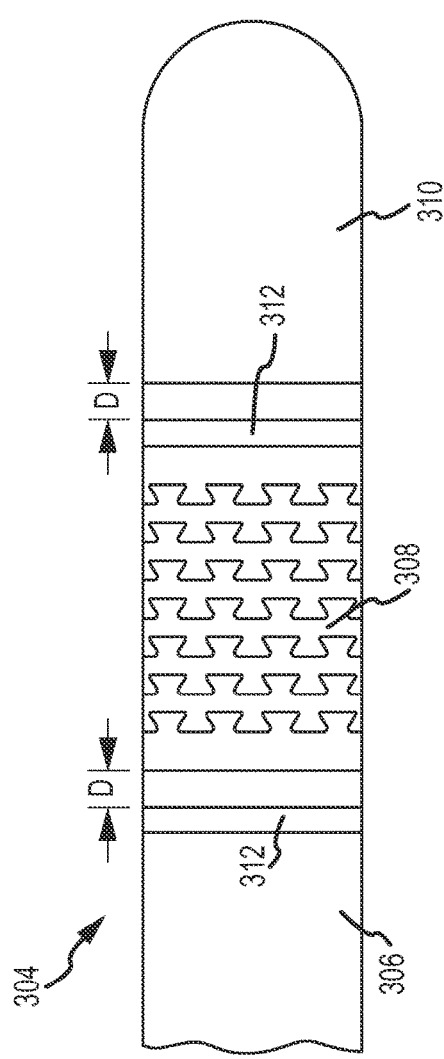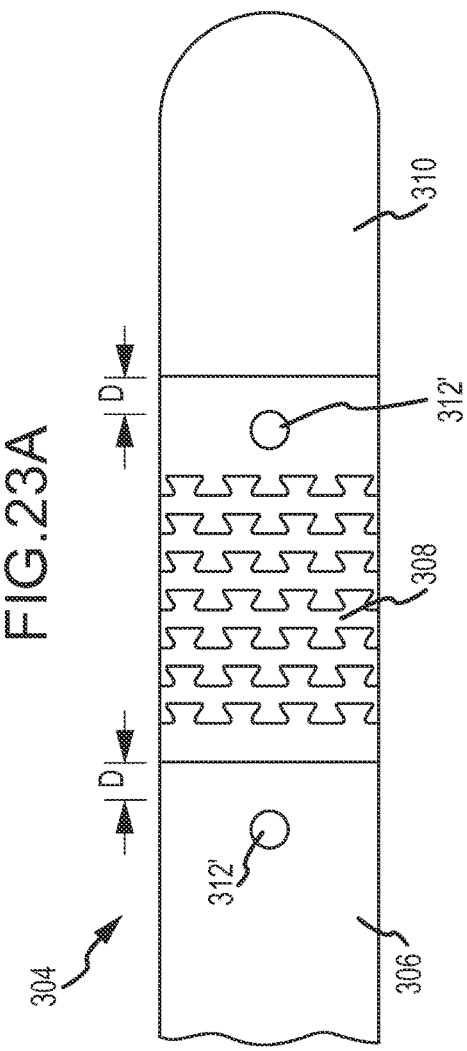

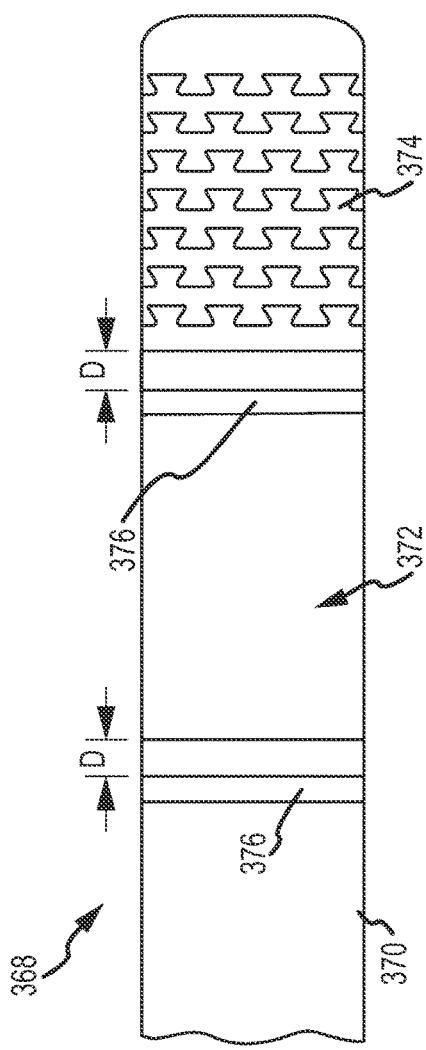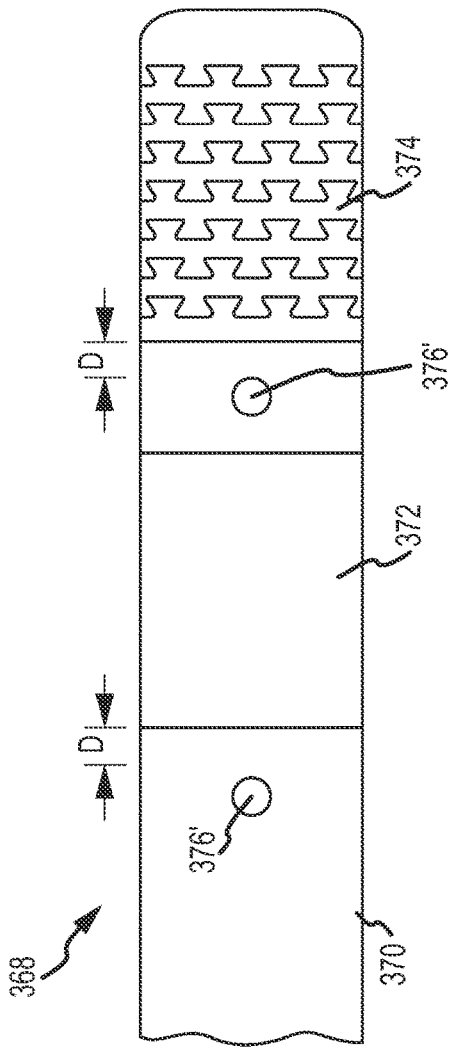

SYSTEM FOR OPTIMIZED COUPLING OF ABLATION CATHETERS TO BODY TISSUES AND EVALUATION OF LESIONS FORMED BY THE CATHETERS

CROSS-REFERENCE TO RELATED APPLICATIONS

This application claims priority to U.S. Provisional Patent Application No. 61/581,247 filed Dec. 29, 2011, the entire disclosure of which is incorporated herein by reference.

BACKGROUND OF THE INVENTION a. Field of the Invention

This invention relates to a system for diagnosis and treatment of tissues in a body. In particular, the instant invention relates to a system for optimizing the degree of mechanical and/or electrical coupling between an ablation catheter and tissue and for evaluating lesions in the tissue created by the ablation catheter.

b. Background Art

It is well known to use ablation catheters to create tissue necrosis in cardiac tissue to correct cardiac arrhythmias (including, but not limited to, atrial fibrillation, atrial flutter, atrial tachycardia and ventricular tachycardia). Arrhythmia can create a variety of dangerous conditions including irregular heart rates, loss of synchronous atrioventricular contractions and stasis of blood flow which can lead to a variety of ailments and even death. It is believed that the primary cause of many arrhythmias is stray electrical signals within one or more heart chambers. The ablation catheter imparts ablative energy (e.g., radiofrequency energy, light energy, ultrasound, or thermal (cryo or heat based) energy) to the heart tissue to create a lesion in the heart tissue. This lesion disrupts undesirable electrical pathways and thereby limits or prevents stray electrical signals that lead to arrhythmias.

Approximately 100 Joules of energy may be adequate to create a lesion in atrial tissue that is sufficient to disrupt an electrical pathway through the tissue. Because clinicians often lack sufficient real-time information regarding the degree of coupling between the ablation catheter and tissue and regarding the lesion being created, however, clinicians regularly apply significantly greater amounts of energy to insure an effective lesion. For example, it is common for clinicians to use a power setting of fifty (50) Watts for sixty (60) seconds thereby applying 3000 Joules of energy to the tissue. The excessive energy application increases several risks associated with ablation therapy including perforation of tissue, coagulation of the blood which can result in creation of a thrombus, and tissue or steam pops resulting from the application of heat to water inside the tissue which may cause the water to boil and burst through the tissue wall.

The inventors herein have recognized a need for a system and method for diagnosis or treatment of tissue within a body that will minimize and/or eliminate one or more of the above-identified deficiencies.

BRIEF SUMMARY OF THE INVENTION

It is desirable to provide a system and method for diagnosis or treatment of tissue in a body. In particular, it is desirable to provide a system for optimizing the degree of mechanical and/or electrical coupling between an ablation catheter and tissue and for evaluating lesions in the tissue created by the ablation catheter.

A system for diagnosis or treatment of tissue in a body in accordance with one embodiment of the invention includes an ablation catheter having a deformable, elongate shaft having proximal and distal ends. The catheter further includes an ablation delivery member disposed proximate the distal end of the shaft. The ablation delivery member is configured to deliver ablation energy to ablate the tissue. The catheter further includes a sensing electrode disposed proximate the ablation delivery member. The sensing electrode is configured to generate a signal indicative of electrical activity in the tissue. The system further includes an electronic control unit configured to control delivery of the ablation energy from the ablation delivery member responsive to the signal.

A system for diagnosis or treatment of tissue in a body in accordance with another embodiment of the invention includes an ablation catheter having a deformable, elongate shaft having proximal and distal ends. The catheter further includes an ablation electrode disposed proximate the distal end of the shaft. The ablation electrode is configured to deliver ablation energy to ablate the tissue and to generate a first signal indicative of electrical activity in the tissue. The catheter further includes a sensing electrode disposed proximate the ablation delivery member. The sensing electrode is configured to generate a second signal indicative of electrical activity in the tissue. The system further includes an electronic control unit configured to control delivery of ablation energy from the ablation electrode responsive to at least one of the first and second signals.

A system in accordance with the present invention is advantageous because the system enables the clinician to optimize the mechanical and/or electrical coupling of the ablation catheter to the tissue thereby improving the efficacy of the delivery of ablative energy. Further, the inventive system enables the clinician to assess the development of lesions in real time. Each of these improvements may contribute to an optimized application of energy to the tissue during ablation thereby reducing the risks of tissue perforation, steam pops and coagulation of the blood.

An ablation catheter in accordance with another embodiment of the present invention includes a distal portion of an elongate shaft, an ablation electrode coupled to a tip portion of the shaft and a first cardiac sensing electrode closely coupled to the shaft. A distal edge of the first cardiac sensing electrode is disposed less than or about one-half millimeter (½ mm) from a proximal edge of the ablation electrode. The catheter further includes a second cardiac sensing electrode closely coupled to the shaft. A distal edge of the second cardiac sensing electrode is disposed less than or about two millimeters (2 mm) from a proximal edge of the first cardiac sensing electrode. The catheter further includes an ablation circuit and a cardiac sensing circuit. The ablation circuit couples to the ablation electrode and the cardiac sensing circuit couples to the first and second cardiac sensing electrodes, respectively and are respectively adapted for simultaneous operation and providing output signals therefrom adapted for near real-time response to lesion growth with receipt by at least one user display screen. In accordance with another embodiment, the catheter further includes a proximity electrical circuit coupled to at least one of the first cardiac sensing electrode, the second cardiac sensing electrode, and the ablation electrode. In accordance with another embodiment, the ablation electrode has a length of between about two millimeters and about four millimeters. In accordance with another embodiment, the ablation electrode comprises two ablation electrodes. In accordance with another embodiment, the catheter further comprises an intermediate ring-type electrode is disposed between the two ablation electrodes and commonly, independently or switchably coupled relative to the two ablation electrodes. In accordance with another embodiment, the ablation electrode comprises a laterally flexible electrode body. In accordance with another embodiment, the ablation electrode comprises an axially flexible electrode body. In accordance with another embodiment, the ablation electrode comprises a laterally and axially flexible electrode body. In accordance with another embodiment, the electrode body is fabricated of a metal and has interlocking complementary members formed around a least a portion of a periphery thereof. In accordance with another embodiment, the catheter further includes an irrigation lumen adapted for coupling a remote source of fluid to the interlocking complementary members. In accordance with another embodiment, the catheter further includes a force transducer coupled to the ablation electrode and a force transducing circuit coupled to the force transducer. In accordance with another embodiment, the force sensor comprises at least one of an optical-based, MEMS-based, piezoelectric-based, electrically (resistively)-based, and capacitively-based force sensor. In accordance with another embodiment, the catheter further includes at least three force sensors disposed in a common lateral plane and spaced evenly apart and wherein each of the at least three force sensors couples to a force sensing circuit. In accordance with another embodiment, the catheter further includes an electro anatomical localization, visualization, and/or orientation system coupled thereto and responsive at least one electroanatomical transducer element coupled to the catheter. In accordance with another embodiment, the electroanatomical transducer element couples to the distal portion of the shaft. In accordance with another embodiment, the electroanatomical transducer element comprises at least one of an impedance-based electrically responsive element coupled to an impedance-based electroanatomical system, a magnetically-based electrically responsive element coupled to a magnetically-based electroanatomical system, an acoustically-based responsive element coupled to an acoustically-based electroanatomical system, and a fluoroscopic-responsive element. In accordance with another embodiment, the ablation electrode comprises an ablation element including at least one of: a radiofrequency ablation element, a laser ablation element, a microwave ablation element, a cryogenic ablation element, and an acoustic ablation element. In accordance with another embodiment, the catheter further includes a plurality of additional cardiac sensing electrodes closely spaced from the first and second cardiac sensing elements. In accordance with another embodiment, a proximity-sensing circuit is coupled to the ablation electrode. In accordance with another embodiment, the proximity-sensing circuit includes a relatively high frequency 'carrier' signal having a frequency above NSR heart rates and typical tachyarrhythmia heart rates.

In accordance with another embodiment, an ablation system includes an electroanatomical system and at least one ablation catheter including at least one tracking element configured to be responsive to or cooperate with the electroanatomical system. The system further includes an ablation element coupled to the tip of the ablation catheter and at least a pair of cardiac sensing elements coupled to a distal portion of the ablation catheter with one of the elements disposed within less than about one millimeter (mm) from a proximal edge of ablation element. The system further includes an ablation circuit coupled to the ablation element and a cardiac sensing circuit coupled to the at least a pair of cardiac sensing elements. The electroanatomical system, the ablation circuit, and the cardiac sensing circuit are configured to operate simultaneously and individually provide respective output signals adapted to be displayed to a system operator. In accordance with another embodiment, the ablation element comprises one of: a radiofrequency ablation element, a laser ablation element, a microwave ablation element, a cryogenic ablation element, and an acoustic ablation element. In accordance with another embodiment, the ablation element comprises a laterally flexible element. In accordance with another embodiment, the ablation element comprises an axially flexible element. In accordance with another embodiment, the ablation element has a length of between about two millimeters and about four millimeters. ablation electrode has a length of between about two millimeters and about four millimeters. In accordance with another embodiment, the ablation element comprises a flexible element having at least two spaced apart flexible elements. In accordance with another embodiment, the at least two spaced apart flexible elements comprise approximately equally dimensioned flexible elements. In accordance with another embodiment, the ablation catheter further includes an intermediate ring electrode disposed between the flexible elements. In accordance with another embodiment, the intermediate ring electrode is commonly electrically coupled to the flexible elements. In accordance with another embodiment, the intermediate ring electrode is electrically coupled for cardiac sensing in cooperation with the at least two cardiac sensing electrodes. In accordance with another embodiment, the system further includes a proximity sensing circuit coupled to the at least one ablation element. In accordance with another embodiment, the system further includes at least one force sensor coupled to the ablation catheter. In accordance with another embodiment, the force sensor comprises at least three force sensors configured in spaced apart relation to provide an output signal related to magnitude and force imparted to the distal tip of the ablation catheter.

A method of monitoring lesion growth in nominally real-time during a cardiac ablation procedure in accordance with one embodiment of the invention includes the step of simultaneously applying ablation energy to a portion of target tissue via an ablation element coupled to the tip of an elongate ablation catheter and providing an output signal related thereto. The method further includes the step of monitoring cardiac activity from a pair of closely situated electrodes with one of the electrodes disposed within about less than about one millimeter (mm) of a proximal edge of the ablation element and providing an output signal related thereto. The method further includes the step of monitoring one of proximity and force imparted to the tip of the elongate ablation catheter and providing a signal related thereto. The method further includes the step of applying energy to a subject with an electroanatomical system to or from an electroanatomical transducer element that results in the ability of the electroanatomical system to determine a three-dimensional (3D) orientation or location of the ablation catheter and provide a 3D visualization output signal related to the 3D orientation or location of the ablation catheter. The method further includes the step of displaying at least one of: the ablation energy signal, the cardiac activity signal, the proximity output signal, the force signal, and the 3D visualization signal. In accordance with another embodiment, the ablation energy comprises energy imparted from one of: a radiofrequency ablation element, a laser ablation element, a microwave ablation element, a cryogenic ablation element, and an acoustic ablation element. In accordance with another embodiment, the ablation element comprises a flexible ablation element. In accordance with another embodiment, the proximity is derived from an electrical resistivity or electrical reactance output signal. In accordance with another embodiment, the force signal is derived from one of an optical signal and a capacitive signal. In accordance with another embodiment, the electroanatomical transducer element comprises at least one of an impedance-based electrically responsive element coupled to an impedance-based electroanatomical system, a magnetically-based electrically responsive element coupled to a magnetically-based electroanatomical system, an acoustically-based responsive element coupled to an acoustically-based electroanatomical system, and a fluoroscopic-responsive element.

Additionally, the present disclosure relates to real-time lesion growth detection in an ablation catheter via closely situated sensing electrodes, flexible ablation tip electrode, and/or proximity sensing techniques during therapy delivery for various arrhythmias, or other tissue ablation procedures. The cardiac ablation embodiments may include closely-spaced cardiac activity sensing electrodes to provide temporal intracardiac electrogram (EGM) information to a clinician. In one form, EGMs may be generated from at least pair of biphasic sensing ring-type electrodes in combination with a tip ablation electrode. The first, or distal, ring electrode may be spaced about one-half millimeter (½ mm) from an adjacent tip ablation electrode adapted for delivery of radiofrequency (RF) ablation energy. In the biphasic sensing embodiment(s) the next adjacent, or proximally adjacent, sensing ring-type electrode may be disposed about 0.25 mm from the first electrode. In the event that orientation of the distal tip portion of a catheter is readily discernible the sensing electrodes can comprise discrete button-type electrodes, ring-type electrodes having insulative coverings selectively covering or revealing conductive portions toward myocardial tissue, or partial ring or other similarly functional electrodes. The ablation electrodes can be adapted to delivery RF energy or other thermally-effective ablation energy (e.g., laser, microwave, cryogenic, acoustic such as high-intensity focused ultrasound, and the like). The ablation electrode or electrodes can also comprise flexible electrodes, of a type such as the Therapy™ Cool Flex™ electrode tip available in select jurisdictions from St. Jude Medical, Inc. Such electrodes are essentially hollow (although a supporting interior coil can be used to both equally distribute irrigant and render the lateral flexing more consistent) and have interlocking members that essentially direct irrigant flow toward a contacted surface while simultaneously squelching irrigant flow away from the surface. More than one such electrode can be employed in tandem with or without an intermediate ring- or band-type electrode to increase the degree of compliance with the surface, including a pulsating endocardial surface. Other flexible electrode types can be employed including so called brush-type electrode and conductive polymer-type electrodes. A supporting shaft can provide pathways for electrical conduit(s), fluid conduit(s), deflection elements, optical elements and the like ultimately wrapped in a biocompatible covering. The electrode tip and/or other electrodes can optionally couple to a sensing circuit for monitoring impedance, complex impedance, reactance and the like so as to provide an indication or index of a degree of tissue coupling (including proximity) to adjacent tissue. In combination the closely-spaced sensing electrodes and the tip electrode, whether traditional rigid or novel flexible types, an EGM obtained during application of ablation energy will promptly indicate loss or reduction of signal amplitude indicating lesion growth passing the sensing electrode pair or success in ablation a desired target tissue region or location. In addition to or in lieu of the proximity sensing capability noted above, a simple or compound force-sensing capability can be used to indicate contact with a surface and a force vector of contact with a surface. The force sensing capability can comprise a single force sensor coupled to the tip electrode with a flexible coupling or, for example, a trio of force sensors to resolve direction and magnitude of contact forces acting on the tip. One or more visualization, localization, and/or orientation sensors can also be coupled to the tip portion of the foregoing catheters to resolve location or orientation in essentially real time without use of ionizing radiation. The EnSite™ system and/or the MediGuide™ technology from St. Jude Medical, Inc. or the Carto™, Carto™ XP, or Carto™ 3 system from Biosense Webster can be used in lieu of or in addition to a fluoroscopic system during an ablation procedure. In the case of impedance-based systems (such as the EnSite™ system), one or more electrodes disposed in or on the catheter couple to receive or emit a carrier signal, such as a multi-frequency signal, from source surface electrodes of the localization system that can be decoded into a three dimensional (3D) location within a patient that is stored or displayed to a user. In the case of magnetic-based systems (such as that enabled by the MediGuide™ technology) one or more metallic, or conductive, coils disposed in or on the catheter similarly allow the 3D location and possibly orientation of the catheter to be resolved, stored, and/or displayed to a user.

Additionally, various medical devices, such as catheters and/or catheter-based systems, are disclosed herein that may include various combinations of features mentioned above and/or disclosed herein to provide additional advantages. For example, in various embodiments, a catheter may include an elongate shaft, a flexible electrode positioned near a distal end of the shaft, and a closely-spaced electrode positioned proximate to the flexible tip electrode. The flexible electrode and the closely-spaced electrode may be configured to ablate tissue and/or sense EGM information from tissue. In at least one embodiment, the closely-spaced electrode may be positioned between about 0.25 mm and about 0.50 mm from the flexible electrode. In at least one embodiment, the closely-spaced electrode may be a ring electrode. Alternatively, in an embodiment, the closely-spaced electrode may be a button-type or spot electrode. Further, in at least one embodiment, the flexible electrode and/or the closely-spaced electrode may be coupled to an electronic control unit (ECU) configured to compute an electrical coupling index (ECI) indicative of a degree of coupling with tissue which may be presented to a clinician on a display or otherwise made available for use in controlling delivery of ablation energy. Additionally, in at least one embodiment, the catheter may include one or more force sensing elements, such as mechanical or optical force sensors, coupled to the flexible electrode and/or the closely-spaced electrode.

Also, in at least one embodiment, the catheter may include at least one irrigation lumen configured to deliver an irrigant, such as saline, through, to, and/or near the flexible electrode and/or the closely-spaced electrode. In such irrigated embodiments, the flexible electrode may include slits or openings configured to allow irrigant to openly flow through at least a portion of the flexible electrode. Additionally or alternatively, the flexible electrode may include a plugged membrane configured to prevent irrigant from flowing out of the flexible electrode and the catheter may also include a return lumen configured to return irrigant from the flexible electrode. Additionally or alternatively, the flexible electrode may include a partially-plugged membrane configured to allow at least some irrigant to flow therethrough and out of the flexible electrode. Additionally or alternatively, the flexible electrode may include an irrigation distribution element configured to direct irrigant along a portion of an exterior surface of the flexible electrode. Additionally or alternatively, the flexible electrode may include a dual or split-flow irrigation element configured to direct irrigant along a portion of an exterior surface of the flexible electrode and along a portion of an exterior surface of the closely-spaced electrode.

Additional combinations of the aforementioned features may be further combined in various embodiments. For example, in at least one embodiment, the catheter may be coupled to an ECU configured to compute an ECI and the catheter may also include one or more force sensing elements, as noted above. Additionally, in at least one embodiment, the catheter may be coupled to an ECU configured to compute an ECI, the catheter may also include one or more force sensing elements, and the catheter may include an irrigation lumen, as noted above. Also, in at least one embodiment, the catheter may include one or more force sensing elements and an irrigation lumen, as noted above. Moreover, in at least one embodiment, the catheter may be coupled to an ECU configured to compute an ECI and the catheter may include an irrigation lumen, as noted above.

In other various embodiments, a catheter may include an elongate shaft, a rigid electrode positioned near a distal end of the shaft, and a closely-spaced electrode positioned proximate to the rigid electrode. The rigid electrode and the closely-spaced electrode may be configured to ablate tissue and/or sense EGM information from tissue. In at least one embodiment, the closely-spaced electrode may be positioned between about 0.25 mm and about 0.50 mm from the rigid electrode. In at least one embodiment, the closely-spaced electrode may be a ring electrode. Alternatively, in an embodiment, the closely-spaced electrode may be a button-type or spot electrode. Further, in at least one embodiment, the ring electrode and/or the closely-spaced electrode may be coupled to an electronic control unit (ECU) configured to compute an electrical coupling index (ECI) indicative of a degree of coupling with tissue which may be presented to a clinician on a display or otherwise made available for use in controlling delivery of ablation energy. Additionally, in at least one embodiment, the catheter may include one or more force sensing elements, such as mechanical or optical force sensors, coupled to the rigid electrode and/or the closely-spaced electrode.

Also, in at least one embodiment, the catheter may include at least one irrigation lumen configured to deliver an irrigant, such as saline, through, to, and/or near the rigid electrode and/or the closely-spaced electrode. In such irrigated embodiments, the rigid electrode may include openings configured to allow irrigant to openly flow through at least a portion of the rigid electrode. Additionally or alternatively, the rigid electrode may include a plugged membrane configured to prevent irrigant from flowing out of the rigid electrode and the catheter may also include a return lumen configured to return irrigant from the rigid electrode. Additionally or alternatively, the rigid electrode may include a partially-plugged membrane configured to allow at least some irrigant to flow therethrough and out of the rigid electrode. Additionally or alternatively, the rigid electrode may include an irrigation distribution element configured to direct irrigant along a portion of an exterior surface of the rigid electrode. Additionally or alternatively, the rigid electrode may include a dual or split-flow irrigation element configured to direct irrigant along a portion of an exterior surface of the rigid electrode and along a portion of an exterior surface of the closely-spaced electrode.

Additional combinations of the aforementioned features may be further combined in various embodiments. For example, in at least one embodiment, the catheter may be coupled to an ECU configured to compute an ECI and the catheter may also include one or more force sensing elements, as noted above. Additionally, in at least one embodiment, the catheter may be coupled to an ECU configured to compute an ECI, the catheter may also include one or more force sensing elements, and the catheter may include an irrigation lumen, as noted above. Also, in at least one embodiment, the catheter may include one or more force sensing elements and an irrigation lumen, as noted above. Moreover, in at least one embodiment, the catheter may be coupled to an ECU configured to compute an ECI and the catheter may include an irrigation lumen, as noted above.

In other various embodiments, a catheter may include an elongate shaft, proximal and distal flexible electrodes positioned near a distal end of the shaft, and a closely-spaced electrode positioned proximate to one of the flexible electrodes. The flexible electrodes and the closely-spaced electrode may be configured to ablate tissue and/or sense EGM information from tissue. In at least one embodiment, the closely-spaced electrode may be positioned between about 0.25 mm and about 0.50 mm from one of the flexible electrodes. In at least one embodiment, the closely-spaced electrode may be a ring electrode. Alternatively, in an embodiment, the closely-spaced electrode may be a button-type or spot electrode. Further, in at least one embodiment, either or both of the flexible electrodes and/or the closely-spaced electrode may be coupled to an electronic control unit (ECU) configured to compute an electrical coupling index (ECI) indicative of a degree of coupling with tissue which may be presented to a clinician on a display or otherwise made available for use in controlling delivery of ablation energy. Additionally, in at least one embodiment, the catheter may include one or more force sensing elements, such as mechanical or optical force sensors, coupled to one or both of the flexible electrodes and/or the closely-spaced electrode.

Also, in at least one embodiment, the catheter may include at least one irrigation lumen configured to deliver an irrigant, such as saline, through, to, and/or near one or both of the flexible electrodes and/or the closely-spaced electrode. In such irrigated embodiments, one or both of the flexible electrodes may include slits or openings configured to allow irrigant to openly flow through at least a portion of the flexible electrode. Additionally or alternatively, one or both of the flexible electrodes may include a plugged membrane configured to prevent irrigant from flowing out of the flexible electrode and the catheter may also include a return lumen configured to return irrigant from the flexible electrode. Additionally or alternatively, one or both of the flexible electrodes may include a partially-plugged membrane configured to allow at least some irrigant to flow therethrough and out of the flexible electrode. Additionally or alternatively, one or both of the flexible electrodes may include an irrigation distribution element configured to direct irrigant along a portion of an exterior surface of the flexible electrode. Additionally or alternatively, one or both of the flexible electrodes may include a dual or split-flow irrigation element configured to direct irrigant along a portion of an exterior surface of the flexible electrode and along a portion of an exterior surface of the closely-spaced electrode.

Additional combinations of the aforementioned features may be further combined in various embodiments. For example, in at least one embodiment, the catheter may be coupled to an ECU configured to compute an ECI and the catheter may also include one or more force sensing elements, as noted above. Additionally, in at least one embodiment, the catheter may be coupled to an ECU configured to compute an ECI, the catheter may also include one or more force sensing elements, and the catheter may include an irrigation lumen, as noted above. Also, in at least one embodiment, the catheter may include one or more force sensing elements and an irrigation lumen, as noted above. Moreover, in at least one embodiment, the catheter may be coupled to an ECU configured to compute an ECI and the catheter may include an irrigation lumen, as noted above.

In other various embodiments, a catheter may include an elongate shaft and a flexible and a rigid electrode positioned near a distal end of the shaft with the flexible electrode located proximal the rigid electrode (and the rigid electrode located distal to the flexible electrode). The catheter may further include a closely-spaced electrode positioned proximate to one of the flexible and rigid electrodes. The flexible and rigid electrodes and the closely-spaced electrode may be configured to ablate tissue and/or sense EGM information from tissue. In at least one embodiment, the closely-spaced electrode may be positioned between about 0.25 mm and about 0.50 mm from one of the flexible or rigid electrodes. In at least one embodiment, the closely-spaced electrode may be a ring electrode. Alternatively, in an embodiment, the closely-spaced electrode may be a button-type or spot electrode. Further, in at least one embodiment, either or both of the flexible and rigid electrodes and/or the closely-spaced electrode may be coupled to an electronic control unit (ECU) configured to compute an electrical coupling index (ECI) indicative of a degree of coupling with tissue which may be presented to a clinician on a display or otherwise made available for use in controlling delivery of ablation energy. Additionally, in at least one embodiment, the catheter may include one or more force sensing elements, such as mechanical or optical force sensors, coupled to one or both of the flexible and rigid electrodes and/or the closely-spaced electrode.

Also, in at least one embodiment, the catheter may include at least one irrigation lumen configured to deliver an irrigant, such as saline, through, to, and/or near one or both of the flexible and rigid electrodes and/or the closely-spaced electrode. In such irrigated embodiments, one or both of the flexible and rigid electrodes may include slits or openings configured to allow irrigant to openly flow through at least a portion of the flexible and/or rigid electrodes. Additionally or alternatively, one or both of the flexible and rigid electrodes may include a plugged membrane configured to prevent irrigant from flowing out of the flexible and/or rigid electrodes and the catheter may also include a return lumen configured to return irrigant from the flexible and/or rigid electrodes. Additionally or alternatively, one or both of the flexible and rigid electrodes may include a partially-plugged membrane configured to allow at least some irrigant to flow therethrough and out of the flexible and/or rigid electrodes. Additionally or alternatively, one or both of the flexible and rigid electrodes may include an irrigation distribution element configured to direct irrigant along a portion of an exterior surface of the flexible and/or rigid electrodes. Additionally or alternatively, one or both of the flexible and rigid electrodes may include a dual or split-flow irrigation element configured to direct irrigant along a portion of an exterior surface of the flexible and/or rigid electrodes and along a portion of an exterior surface of the closely-spaced electrode.

Additional combinations of the aforementioned features may be further combined in various embodiments. For example, in at least one embodiment, the catheter may include a closely-spaced electrode positioned proximate to one of the flexible and rigid electrodes, be coupled to an ECU configured to compute an ECI and may also include one or more force sensing elements, as noted above. Additionally, in at least one embodiment, the catheter may be coupled to an ECU configured to compute an ECI, the catheter may also include one or more force sensing elements, and the catheter may include an irrigation lumen, as noted above. Also, in at least one embodiment, the catheter may include one or more force sensing elements and an irrigation lumen, as noted above. Moreover, in at least one embodiment, the catheter may be coupled to an ECU configured to compute an ECI and the catheter may include an irrigation lumen, as noted above.

In other various embodiments, a catheter may include an elongate shaft and a flexible and a rigid electrode positioned near a distal end of the shaft with the rigid electrode located proximal the flexible electrode (and the flexible electrode located distal to the rigid electrode). The catheter may further include a closely-spaced electrode positioned proximate to one of the flexible and rigid electrodes. The flexible and rigid electrodes and the closely-spaced electrode may be configured to ablate tissue and/or sense EGM information from tissue. In at least one embodiment, the closely-spaced electrode may be positioned between about 0.25 mm and about 0.50 mm from one of the flexible or rigid electrodes. In at least one embodiment, the closely-spaced electrode may be a ring electrode. Alternatively, in an embodiment, the closely-spaced electrode may be a button-type or spot electrode. Further, in at least one embodiment, either or both of the flexible and rigid electrodes and/or the closely-spaced electrode may be coupled to an electronic control unit (ECU) configured to compute an electrical coupling index (ECI) indicative of a degree of coupling with tissue which may be presented to a clinician on a display or otherwise made available for use in controlling delivery of ablation energy. Additionally, in at least one embodiment, the catheter may include one or more force sensing elements, such as mechanical or optical force sensors, coupled to one or both of the flexible and rigid electrodes and/or the closely-spaced electrode.

Also, in at least one embodiment, the catheter may include at least one irrigation lumen configured to deliver an irrigant, such as saline, through, to, and/or near one or both of the flexible and rigid electrodes and/or the closely-spaced electrode. In such irrigated embodiments, one or both of the flexible and rigid electrodes may include slits or openings configured to allow irrigant to openly flow through at least a portion of the flexible and/or rigid electrodes. Additionally or alternatively, one or both of the flexible and rigid electrodes may include a plugged membrane configured to prevent irrigant from flowing out of the flexible and/or rigid electrodes and the catheter may also include a return lumen configured to return irrigant from the flexible and/or rigid electrodes. Additionally or alternatively, one or both of the flexible and rigid electrodes may include a partially-plugged membrane configured to allow at least some irrigant to flow therethrough and out of the flexible and/or rigid electrodes. Additionally or alternatively, one or both of the flexible and rigid electrodes may include an irrigation distribution element configured to direct irrigant along a portion of an exterior surface of the flexible and/or rigid electrodes. Additionally or alternatively, one or both of the flexible and rigid electrodes may include a dual or split-flow irrigation element configured to direct irrigant along a portion of an exterior surface of the flexible and/or rigid electrodes and along a portion of an exterior surface of the closely-spaced electrode.

Additional combinations of the aforementioned features may be further combined in various embodiments. For example, in at least one embodiment, the catheter may include a closely-spaced electrode positioned proximate to one of the flexible and rigid electrodes, be coupled to an ECU configured to compute an ECI and may also include one or more force sensing elements, as noted above. Also, in at least one embodiment, the catheter may be coupled to an ECU configured to compute an ECI and the catheter may include an irrigation lumen, as noted above. Additionally, in at least one embodiment, the catheter may be coupled to an ECU configured to compute an ECI, the catheter may also include one or more force sensing elements, and the catheter may include an irrigation lumen, as noted above. Also, in at least one embodiment, the catheter may include one or more force sensing elements and an irrigation lumen, as noted above. Moreover, in at least one embodiment, the catheter may be coupled to an ECU configured to compute an ECI and the catheter may include an irrigation lumen, as noted above. Additionally, in at least one embodiment, the catheter may include a closely-spaced electrode positioned proximate to one of the flexible and rigid electrodes, be coupled to an ECU configured to compute an ECI and may also include an irrigation lumen, as noted above.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 4 is a perspective view of another embodiment of an ablation catheter for use in the system of FIG. 1.

FIG. 5 is a cross-sectional view of the ablation catheter of FIG. 4.

FIGS. 11A-B are plan views of another embodiment of an ablation catheter for use in the system of FIG. 1.

FIG. 12 is a diagrammatic view of another embodiment of the catheter of FIGS. 11A-B.

FIGS. 15A-B are plan views of another embodiment of an ablation catheter for use in the system of FIG. 1.

FIG. 16 is a diagrammatic view of another embodiment of the catheter of FIGS. 15A-B.

FIGS. 23A-B are plan views of another embodiment of an ablation catheter for use in the system of FIG. 1.

FIGS. 27A-B are plan views of another embodiment of an ablation catheter for use in the system of FIG. 1.

DETAILED DESCRIPTION OF EMBODIMENTS OF THE INVENTION

Figure 1:
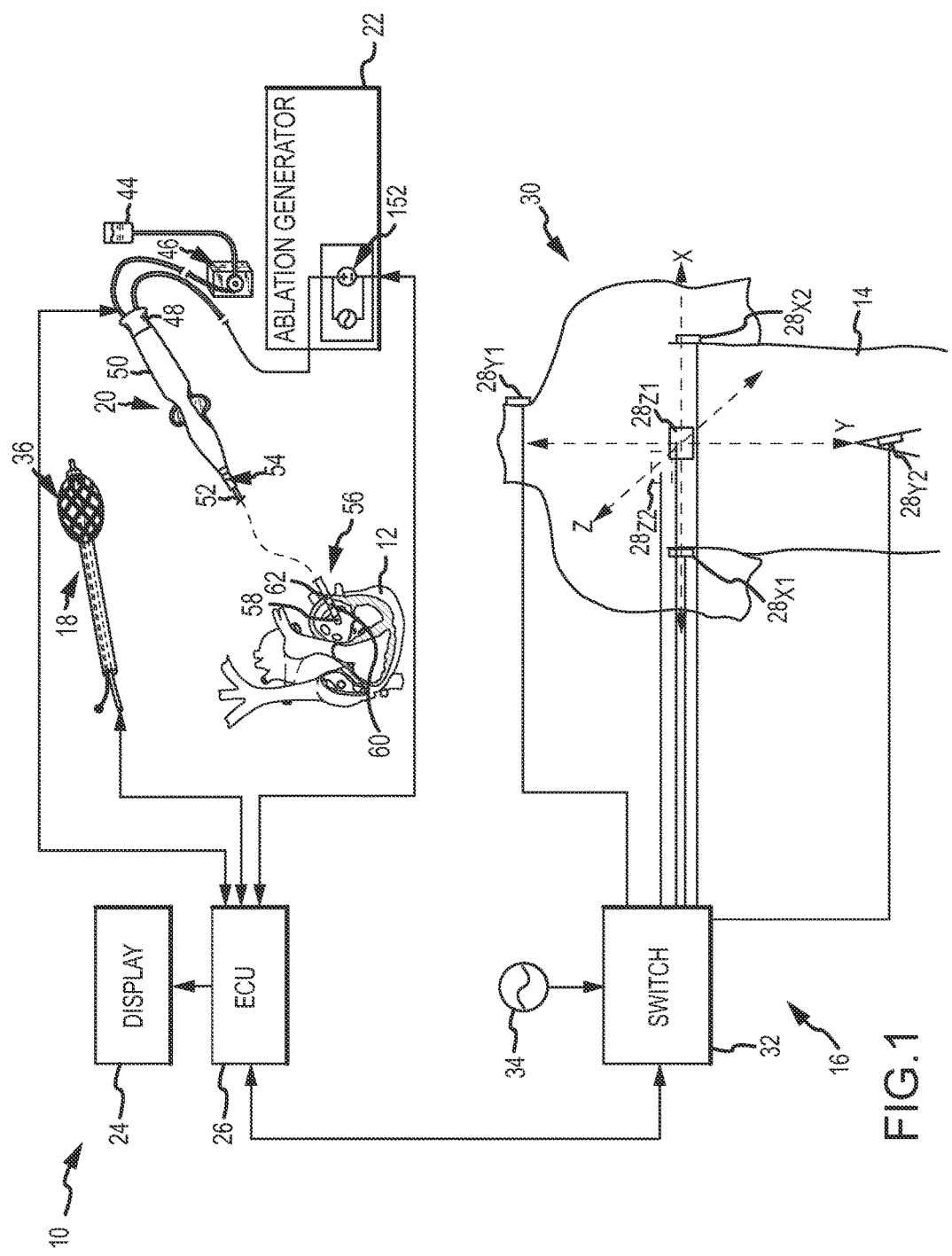
FIG. 1 is a diagrammatic view of a system for diagnosis or treatment of tissue in a body in accordance with one embodiment of the present invention.

Referring now to the drawings wherein like reference numerals are used to identify identical or similar components in the various views, FIG. 1 illustrates a system 10 for diagnosis or treatment of tissue 12 in a body 14 in accordance with one embodiment of the invention. In the illustrated embodiment tissue 12 comprises cardiac tissue and body 14 comprises a human body. It should be understood, however, that a system 10 in accordance with the present teachings may find application in connection with procedures for the diagnosis or treatment of a variety of tissues in human and non-human bodies. System 10 may include a medical device position and navigation system 16, one or more medical devices including, for example, an electrophysiological (EP) mapping catheter 18 and an ablation catheter 20, an ablation generator 22, a display system 24, and an electronic control unit (ECU) 26.

Medical device position and navigation system 16 is provided to determine the position and orientation of medical devices within body 14 such as catheters 18, 20 and may also be used to generate an electrophysiological map of a region of interest. System 16 may display geometries or models of a region of interest in body 14 on a display such as display system 24 along with representations of catheters 18, 20 indicative of the position of catheters 18, 20 relative to the region of interest. System 16 may also display activation timing and voltage data for cardiac tissue on the same display system 24.

System 16 may comprise a system that employs electric fields to detect the position of catheters 18, 20 within body 14 and may, for example, comprise the system available under the trademark "ENSITE NAVX" (a/k/a EnSite Classic as well as newer version of the EnSite system denoted as ENSITE VELOCITY") by St. Jude Medical, Inc. and generally shown in U.S. Pat. No. 7,263,397 titled "Method and Apparatus for Catheter Navigation and Location Mapping in the Heart," the entire disclosure of which is incorporated herein by reference. System 16 is based on the principle that when low amplitude electrical signals are passed through the thorax, body 14 acts as a voltage divider (or potentiometer or rheostat) such that the electrical potential or field strength measured at electrodes on catheters 18, 20 may be used to determine the position of the electrode, and therefore catheters 18, 20, relative to a pair of external patch electrodes using Ohm's law and the relative location of a reference electrode (e.g. in the coronary sinus).

In one configuration, system 16 includes three pairs of patch electrodes 28 (namely $28_{X1}$, $28_{X2}$, $28_{Y1}$, $28_{Y2}$, $28_{Z1}$, $28_{Z2}$) that are placed on opposed surfaces of body 14 (e.g., chest and back, left and right sides of the thorax, and neck and leg) and form generally orthogonal x, y, and z axes as well as a reference electrode/patch (not shown) that is typically placed near the stomach and provides a reference value and acts as the origin of a coordinate system 30 for the system 16. Electrodes 28 are used to create axes specific electric fields within body 14. Electrodes $28_{X1}$, $28_{X2}$ may be placed along a first (x) axis. Similarly, electrodes $28_{Y1}$, $28_{Y2}$ may be placed along a second (y) axis, and electrodes $28_{Z1}$, $28_{Z2}$ may be placed along a third (z) axis. Each of the electrodes 28 may be coupled to a multiplex switch 32. ECU 26 is configured through appropriate software to provide control signals to switch 32 and thereby sequentially couple pairs of electrodes 28 to a signal generator 34. Sinusoidal currents are driven through each pair of patch electrodes 28 to generate an electromagnetic field within body 14 and voltage measurements for one or more position sensors (e.g., electrodes) associated with catheters 18, 20 are obtained. The measured voltages are a function of the distance of the position sensors from the patch electrodes 28. The measured voltages are compared to the potential at the reference electrode and a position of the position sensors within the coordinate system 30 of the navigation system 16 is determined.

In an alternative embodiment, system 16 may comprise a system that employs magnetic fields to detect the position of catheters 18, 20 within body 14 such as the system available under the trademark "GMPS" or "MEDIGUIDE" by St. Jude Medical, Inc. and generally shown and described in, for example, U.S. Pat. No. 6,233,476 titled "Medical Positioning System," U.S. Pat. No. 7,197,354 titled "System for Determining the Position and Orientation of a Catheter," and U.S. Pat. No. 7,386,339 titled "Medical Imaging and Navigation System," the entire disclosures of which are incorporated herein by reference or the system available under the trademark "CARTO XP" by Biosense Webster, Inc. and generally shown and described in, for example, U.S. Pat. No. 5,391,199 titled "Apparatus and Method for Treating Cardiac Arrhythmias," U.S. Pat. No. 5,443,489 titled "Apparatus and Method for Ablation," U.S. Pat. No. 5,558,091 titled "Magnetic Determination of Position and Orientation," U.S. Pat. No. 6,498,944 titled "Intrabody Measurement," U.S. Pat. No. 6,788,967 titled "Medical Diagnosis, Treatment and Imaging Systems," and U.S. Pat. No. 6,690,963 titled "System for Determining the Location and Orientation of an Invasive Medical Instrument," the entire disclosures of which are incorporated herein by reference. In such a system, a magnetic field generator may be employed having three orthogonally arranged coils, arranged to create a magnetic field within body 14 and to control the strength, orientation, and frequency of the field. The magnetic field generator may be located above or below the patient (e.g., under a patient table) or in another appropriate location. Magnetic fields are generated by the coils and current or voltage measurements for one or more position sensors (e.g., a coil) associated with catheters 18, 20 are obtained. The measured currents or voltages are proportional to the distance of the sensors from the coils thereby allowing a position of the sensors within the coordinate system 30 of system 16. In yet another alternative embodiment, system 16 may comprise a combination electric-field and magnetic-field based system such as the system available under the trademark "CARTO 3" by Biosense Webster, Inc. and generally shown with reference to U.S. Pat. No. 7,536,218 titled "Hybrid Magnetic-Based and Impedance-Based Position Sensing," and U.S. Pat. No. 7,848,789 titled "Hybrid Magnetic-Based and Impedance-Based Position Sensing," the entire disclosures of which are incorporated herein by reference. Alternatively still, system 16 may comprise an acoustic system such as the system generally shown with reference to U.S. Pat. No. 6,751,492 titled "System for Mapping a Heart Using Catheters Having Ultrasonic Position Sensors," the entire disclosure of which is incorporated herein by reference.

EP mapping catheter 18 is provided for use in gathering EP data associated with tissue 12. Catheter 18 includes a plurality of EP mapping electrodes 36. The electrodes 36 are placed in the body 14 (e.g., within the heart) within electrical fields created by exciting patch electrodes 28. The electrodes 36 experience voltages that are dependent on the location between the patch electrodes 28 and the position of the electrodes 36 relative to the surface of tissue 12. Voltage measurement comparisons made between electrodes 36 can be used to determine the position of the electrodes 36 relative to tissue 12. Movement of the electrodes 36 within the heart (e.g., within a heart chamber) produces information regarding the geometry of the heart as well as EP data. For example, voltage levels on the tissue surface over time may be projected on the image of the geometry of the heart as an activation map. The voltage levels may be represented in various colors and the EP data may be animated to show the passage of electromagnetic waves over the tissue surface. Information received from the electrodes 36 can also be used to display the location and orientation of the electrodes 36 and/or the tip of EP catheter 18 relative to the tissue 12.

Figure 2:
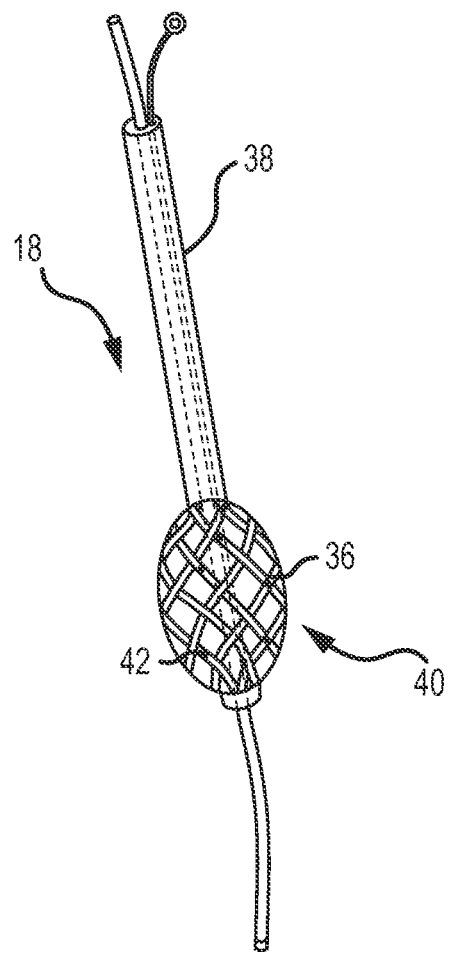
FIG. 2 is a perspective view of one embodiment of an electrophysiological mapping catheter for use in the system of FIG. 1.

EP catheter 18 may be a non-contact mapping catheter such as the catheter available from St. Jude Medical, Atrial Fibrillation Division, Inc. under the registered trademark "ENSITE ARRAY." It should be understood, however, that the present invention may also be used with contact mapping systems in which measurements are taken through contact of electrodes with the tissue surface. Referring to FIG. 2, catheter 18 includes a deformable tubular body 38 including a deformable distal portion 40. Portion 40 may be formed as a braid of insulated wires 42 with an array of mapping electrodes 36 formed where the insulation on the wires 42 has been removed. Portion 40 may be deformed by expansion (e.g. through use of a balloon) into a stable and reproducible geometric shape to fill a space (e.g., a portion of a heart chamber) after introduction into the space. One or more reference electrodes (not shown) may also be located nearer the distal end of catheter 18 than electrodes 36 and may contact the tissue surface to calibrate the electrode array and maintain the position of the electrode array. An exemplary EP catheter is shown in commonly assigned U.S. Pat. No. 7,289,843 titled "Software for Mapping Potential Distribution of a Heart Chamber," the entire disclosure of which is incorporated herein by reference.

Referring again to FIG. 1, ablation catheter 20 is provided for examination, diagnosis and treatment of internal body tissues such as tissue 12. In accordance with one embodiment of the invention, catheter 20 comprises an irrigated radio-frequency (RF) ablation catheter. It should be understood, however, that catheter 20 is provided for illustration only and that system 10 could be adapted for use with a variety of ablation catheters including those providing different types of ablation energy (e.g., cryoablation, microwave, laser, acoustic, such as high intensity focused ultrasound (HIFU), etc.). Catheter 20 is connected to a fluid source 44 having a biocompatible fluid such as saline through a pump 46 (which may comprise, for example, a fixed rate roller pump or variable volume syringe pump with a gravity feed supply from fluid source 44 as shown) for irrigation. Fluid source 44 and/or pump 46 may comprise the unit available under the trademark "COOL PONT" from St. Jude Medical, Inc. Catheter 20 is also electrically connected to ablation generator 22 for delivery of RF energy. Catheter 20 may include a cable connector or interface 48, a handle 50, a shaft 52 having a proximal end 54 and a distal end 56 (as used herein, "proximal" refers to a direction toward the end of the catheter near the clinician, and "distal" refers to a direction away from the clinician and (generally) inside the body of a patient), one or more ablation delivery members 58, one or more position sensors 60 and one or more sensing electrodes 62. Catheter 20 may also include other conventional components not illustrated herein such as a temperature sensor, additional electrodes, and corresponding conductors or leads. Catheter 20 may further include signal processing circuitry and may include a memory accessible upon connection to ECU 26 or another means for providing identifying information for catheter 20 (e.g., catheter manufacturer, model or type, potential configurations for catheter 20, etc.) to ECU 26.

Connector 48 provides mechanical, fluid and electrical connection(s) for cables extending to pump 46 and ablation generator 22 Connector 48 is conventional in the art and is disposed at a proximal end of catheter 20.

Handle 50 provides a location for the clinician to hold catheter 20 and may further provide means for steering or guiding shaft 52 within body 14. For example, handle 50 may include means to move a guidewire extending through catheter 20 to distal end 56 of shaft 52 to steer distal end 56 and, thus, shaft 52. Handle 50 is also conventional in the art and it will be understood that the construction of handle 50 may vary and may be absent in a fully-robotic implementation of the system.

Shaft 52 is an elongated, flexible member configured for movement within body 14. Shaft 52 supports ablation delivery member 58, position sensors 60, and sensing electrodes 62, associated conductors, and possibly additional electronics used for signal processing or conditioning. Shaft 52 may also permit transport, delivery, and/or removal of fluids (including irrigation fluids and bodily fluids), medicines, and/or surgical tools or instruments. Shaft 52 may be made from conventional materials such as polyurethane and defines one or more lumens configured to house and/or transport electrical conductors, fluids, or surgical tools. Shaft 52 may be introduced into a blood vessel or other structure within body 14 through a conventional introducer sheath. Shaft 52 may then be steered or guided through body 14 to a desired location such as tissue 12 using guide wires or with pullwires or other means known in the art including remote catheter guidance systems (RCGS) such as a system or systems described and illustrated in U.S. Published Patent Application No. 20090247942 published Oct. 1, 2009 and titled "Robotic Catheter Manipulator Assembly"; U.S. Published Patent Application No. 20090247944 published Oct. 1, 2009 and titled "Robotic Catheter Rotatable Device Cartridge"; U.S. Published Patent Application No. 20090247993 published Oct. 1, 2009 and titled "Robotic Catheter System"; U.S. Published Patent Application No. 20090248042 published Oct. 1, 2009 and titled "Model Catheter Input Device"; International Published Patent Application No. WO 2009/120982 published Oct. 1, 2009 and titled "Robotic Catheter System With Dynamic Response"; U.S. Published Patent Application No. 20100256558 published Oct. 7, 2011 and titled "Robotic Catheter System"; and U.S. patent application Ser. No. 12/933,063 filed Sep. 16, 2010 and titled "Robotic Catheter System Input Device", the entire disclosures of which are incorporated herein by reference.

Ablation delivery member 58 is provided to deliver ablation energy to tissue 12 to create ablative lesions in tissue 12 and thereby disrupt stray electrical pathways in tissue 12. Member 58 is disposed proximate distal end 56 of shaft 52 (and may be disposed at a distal tip of shaft 52) and may be configured in a variety of ways depending on, among other things, the type of ablative energy to be delivered by member 58.

Figure 3:
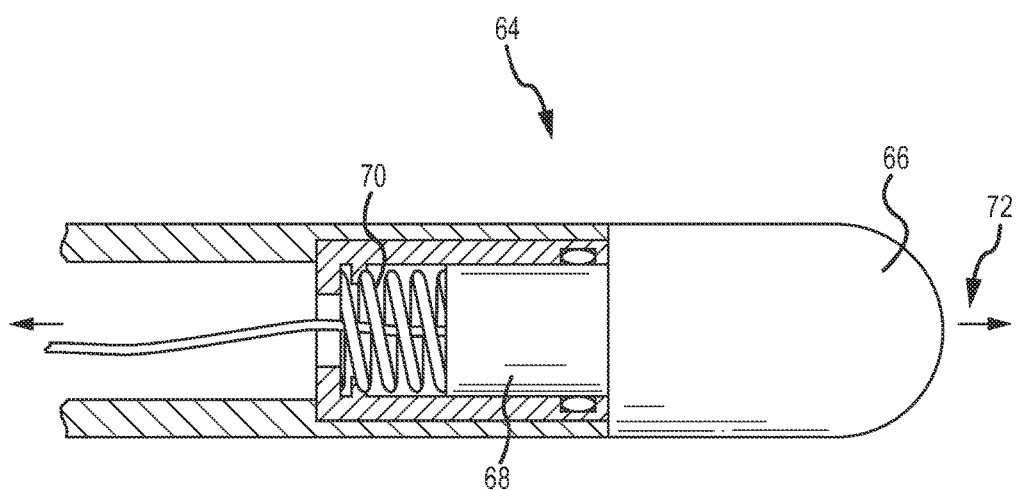
FIG. 3 is a cross-sectional view of one embodiment of an ablation catheter for use in the system of FIG. 1.

In accordance with one embodiment of the invention, ablation delivery member 58 may comprise an electrode configured to deliver radio frequency ablation energy. In accordance with another embodiment of the invention, the electrode may be rigid such that the electrode is resistant of bending along the length of the electrode between the proximal and distal ends of the electrode. Referring to FIG. 3, for example, in one embodiment an ablation catheter 64 may be provided having a rigid electrode 66 disposed at a distal end of a shaft of the catheter 64. Electrode 66 may be made from conductive materials including metals such as platinum, iridium, gold, and silver and metal alloys including stainless steel and Nitinol. Electrode 66 may include a rounded tip at a distal end for atraumatic engagement of tissue 12 and a reduced diameter stem 68 at a proximal end that is received within the distal end of the catheter shaft and engaged by a spring 70 for movement along a longitudinal axis 72 extending through electrode 66. Further information regarding catheter 64 and electrode 66 may be found in U.S. Pat. No. 5,951,471 titled "Catheter-based Coronary Sinus Mapping and Ablation," the entire disclosure of which is incorporated herein by reference.

In accordance with another embodiment of the invention, the electrode comprising ablation delivery member 58 may be a flexible electrode such that the electrode is configured to bend along the length of the electrode between the proximal and distal ends of the electrode. The flexibility of the electrode improves mechanical coupling of the electrode to tissue 12 by increasing the surface area engagement thereby also improving electrical coupling of the catheter to tissue 12. Such flexible electrodes may be made from conductive flexible polymers or may comprise brush-type electrodes.

Figure 6:
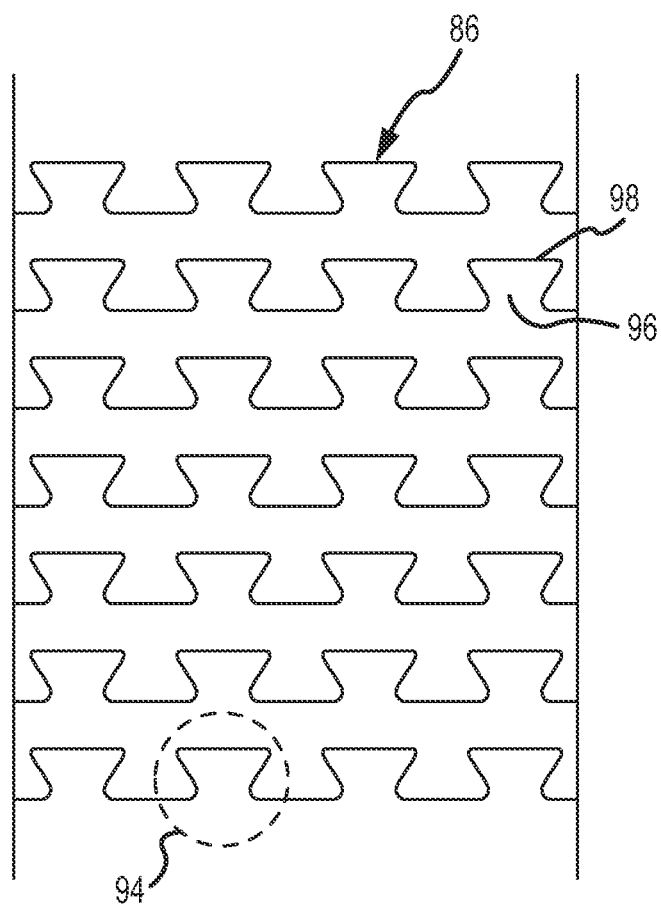
FIG. 6 is a plan view of a portion of the ablation catheter of FIG. 4.

Referring to FIGS. 4 and 5, one embodiment of an ablation catheter 74 usable with system 10 may include a flexible electrode of the type used in the ablation catheter available under the trademark "THERAPY COOLFLEX" from St. Jude Medical, Inc. In the illustrated embodiment, catheter 74 includes a pair of electrodes 76, 78 functioning as ablation delivery members. It should be understood, however, that a single electrode may alternatively be used to deliver ablation energy to tissue 12. Electrodes 76, 78 are configured to bend along a longitudinal axis 80 extending through the catheter shaft and electrodes 76, 78. Electrodes 76, 78 may, for example, be configured to bend between 0.2 degrees and 70 degrees relative to axis 80 and preferably between 5 degrees and 45 degrees relative to axis 80. Electrodes 76, 78, may be further configured to deform when engaging tissue 12 such that the cross-sectional shape of electrodes 76, 78, changes and may also be configured to shorten when pressed against tissue 12. Electrodes 76, 78, may be made from a variety of conductive and biocompatible materials including natural and synthetic polymers, metals, metal alloys—including Nitinol and the alloy sold under the registered trademark "MP35N" by SPS Technologies, Inc.—and textile fibers. Referring to FIG. 5, electrodes 76, 78, are cylindrical and define central lumens 82, 84, respectively. Electrode 76 may define a rounded tip at a distal end for atraumatic engagement of tissue 12. Electrodes 76, 78 both include one or more elongate slits 86 (see FIG. 6) extending generally radially through either all of the thickness of the electrode wall 88 (in the form of passages beginning at a radially outer surface 90 of each electrode wall 88 through to a radially inner surface 92 of each electrode wall 88) or a portion of the thickness of the electrode wall 88 (in the form of grooves beginning at radially outer surface 90 of wall 88 to a point between the radially outer and inner surfaces 90, 92 of wall 88). Slits 86 may form a continuous loop (to form a generally-helical shape) or loops or may be discontinuous. Slits 86 may be equidistant from each other or at unequal distances. Referring to FIG. 6, in the illustrated embodiment, slits 86 form an outline defining a plurality of interlocking blocks 94 with each block 94 having a neck 96 and a head 98 that is wider than neck 96 such that the head 98 of one bock 94 is disposed between the necks 96 of two adjacent blocks 94 and axial movement of the each head 98 is limited by the heads 98 of the adjacent blocks 94. Although slits 86 are configured to form dove-tailed interlocking blocks 94 in the illustrated embodiment, slits 86 may be formed in various shapes, sizes and configurations including, e.g. straight lines, zig zags, undulating lines and wavy lines. The slits 86 may have a width between 0.01 and 0.5 millimeters and may be of a size sufficient to permit shortening and lengthening of electrodes 76, 78 along axis 80. Electrodes 76, 78 may include coils 100, 102 in lumens 82, 84 to provide structural integrity. Coils 100, 102, may also bias electrodes 76, 78, to a predetermined configuration (e.g., straight or curved) and length. An irrigation tube 104 may also extend from a fluid source such as source 44 (seen in FIG. 1) through lumens 82, 84 and disperse irrigation fluid to electrodes 76, 78 for passage through slits 86 where slits 86 comprises passages. The configuration of slits 86 will result in irrigant flow being directed toward the contact interface with tissue 12 (where slits will be spread further apart upon bending of electrodes 76, 78) while irrigant flow away from the contact interface is limited (where slits will be compressed upon bending of electrodes 76, 78). Further information regarding catheter 74 and electrodes 76, 78 and/or related structures may be found in one or more of the following applications: U.S. Published Patent Application No. 2008/0294158 titled "Ablation Catheter With Flexible Tip and Methods of Making the Same"; U.S. Published Patent Application No. 2010/0152731 titled Flexible Tip Catheter With Extended Fluid Lumen"; U.S. Published Patent Application No. 2011/0288392 titled "Kit for Non-Invasive Electrophysiology Procedures and Methods of Its Use," U.S. Published Patent Application No. 2011/0313417 titled "Ablation Catheter Having Flexible Tip With Multiple Flexible Electrode Segments," International Published Patent Application No. WO 2011/159861 titled "Ablation Catheter Having Flexible Tip With Multiple Flexible Electrode Segments" and International Published Patent Application No. WO 2011/159955 titled "Catheter Having Flexible Tip With Multiple Flexible Segments," the entire disclosures of which are incorporated herein by reference.

Although specific exemplary catheters and ablation delivery members have been discussed hereinabove, it should be understood that a variety of catheters could be employed in connection with the invention. For example, although FIGS. 4-5 illustrate a catheter 74 with two flexible electrodes 76, 78 functioning as ablation delivery elements, a catheter could be employed with ablation delivery elements comprising one or more flexible electrodes, such as one of electrodes 76, 78, and one or more rigid electrodes, such as electrode 66 in catheter 64 shown in FIG. 3 or a ring type electrode. In the case of a catheter with two ablation delivery members spaced longitudinally along the catheter shaft, the distal electrode may comprise a flexible electrode while the more proximal electrode comprises a rigid electrode. Alternatively, the more distal electrode may comprise a rigid electrode and the more proximal electrode comprise a flexible electrode.

Figure 7:
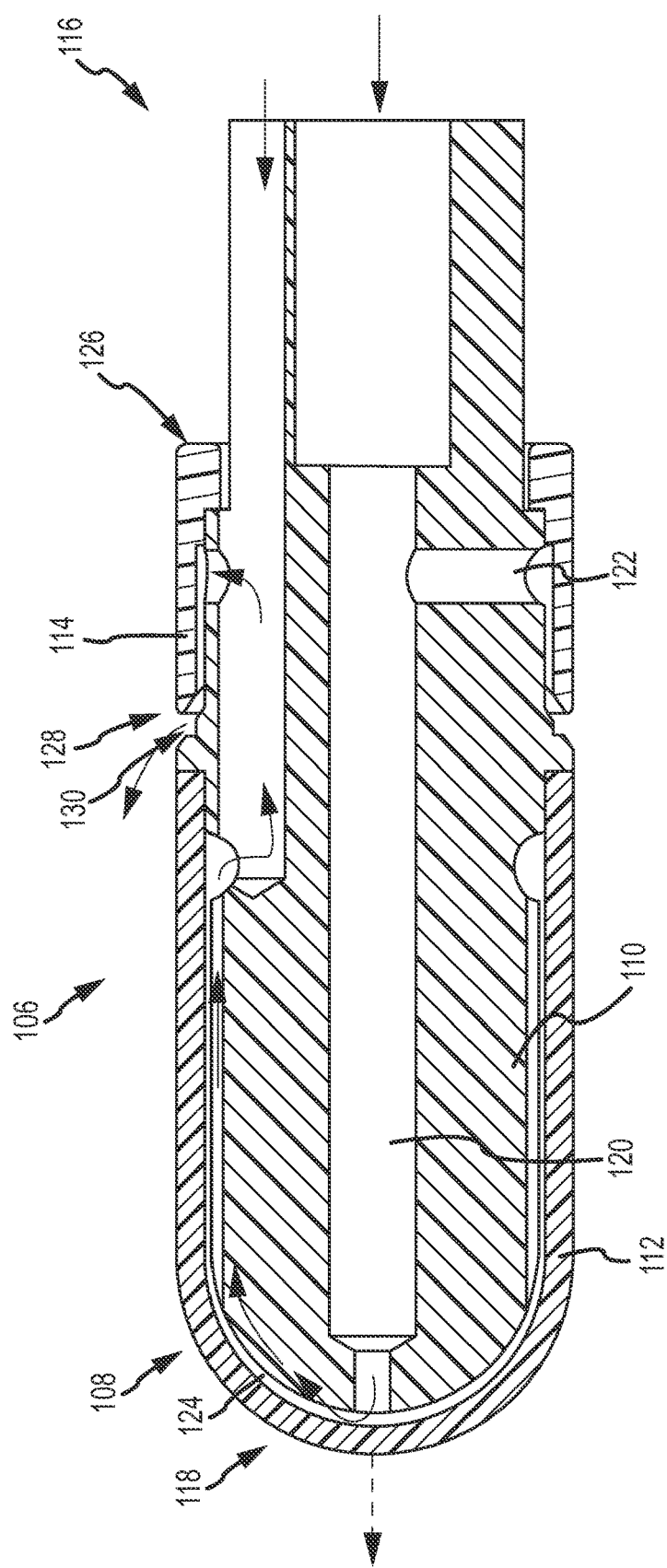
FIG. 7 is a cross-sectional view of another embodiment of an ablation catheter for use in the system of FIG. 1 illustrating an exemplary irrigation system.

Ablation delivery members 58 may include an irrigation system to control temperature in and/or near delivery members 58 in order to reduce tissue charring, steam pops, and blood coagulation while enabling formation of deeper lesions in tissue 12. The irrigation system may be a closed system in which a biocompatible irrigating fluid such as saline flows only within one or more cavities within delivery member 58 or an open irrigation system in which irrigating fluid flows outward from delivery member 58 to an outer surface of the delivery member 58 and to tissue 12. Referring to FIG. 7, in accordance with one embodiment, a catheter 106 is provided having an ablation delivery member 108 including inner and outer members 110, 112 and an irrigation distribution element 114.

Inner member 110 is received within outer member and defines a fluid manifold. Inner member 110 includes a proximal end 116 and a distal end 118. Proximal end 116 may be configured to receive a fluid delivery tube extending through the shaft of the catheter 106. Inner member 110 may be made from a material that is electrically non-conductive and thermally non-conductive or at least less conductive than outer member 112, such as polyether ether ketone (PEEK), high density polyethylene (HDPE), ceramics or other known materials. Inner member 110 may define a plurality of fluid passages including an axially extending passage 120 and one or more radially extending passages 122 in the illustrated embodiment. Radially extending passages 122 may be angled relative to the longitudinal axis of inner member 110 and may be equally spaced. The diameter of the passages 120, 122 may also vary throughout the length of the passages in order to realize an optimal fluid flow as described in U.S. Published Patent Application No. 2008/0249522 titled "Irrigated Catheter With Improved Fluid Flow," the entire disclosure of which is incorporated herein by reference. A portion or all of passages 120, 122 may also be coated with a non-conductive material such as polytetrafluoroethylene commonly sold under the trademark "TEFLON" by E.I. Du Pont de Nemours and Co. Inner member 110 may further define a plurality of channels on a radially outer surface configured to receive temperature sensors such as thermocouples or thermistors.

Outer member 112 may provide ablation energy to tissue 12. Member 112 may be relatively thin to mitigate temperature gradients across delivery member 108 and the effect of orientation on temperature measurements. Outer member 112 may be made from electrically conductive materials including metals such as gold, platinum, iridium, and palladium or metal alloys such as stainless steel and is connected to ablation generator 22 and/or ECU 26 by one or more conductors extending from member 112 through the catheter shaft. Outer member 112 may be connected to inner member 110 in a variety of conventional ways including but not limited to adhesive bonding, press-fit or snap-fit configurations, mechanical deformation or ultrasonic staking. Outer member 112 may include a number of grooves or slots (not shown) to divide member 112 into a plurality of segments each of which corresponds to a different temperature sensor. In accordance with the illustrated embodiment, outer member 112 combines with inner member 110 to define a space 124 therebetween that interrupts or reduces the heat transfer path between members 110, 112 and between the temperature sensors. The configuration of space 124 can vary and may be regular or irregular and include support members (e.g., flutes, bosses, posts and the like). In the illustrated embodiment, irrigating fluid flows through space 124 to absorb heat from the circulating blood pool and the lesion being created in tissue 12. In alternative embodiments, space 124 comprises a vacuum region or evacuated region acting as an insulator to reduce convection heat transfer.

Irrigation distribution element 14 may comprise an annular member disposed about inner member 110 proximal to outer member 112. Element 114 may have an outer diameter that is the same or substantially the same as the outer diameter of outer member 112. Element 114 defines a proximal end 126 and a distal end 128. Proximal end 126 may engage the distal end of the catheter shaft. The distal end 128 of element 114 defines a circumferential irrigation port 130 that is configured to guide irrigation fluid about and along the outer surface of member 112.

In operation, irrigation fluid is received near proximal end 116 of member 108 from a fluid delivery tube. The fluid flows along axial passage 120. A portion of the fluid passes through radial passage 122 and outward through port 130. Another portion of the fluid continues along axial passage 120 until it exits a port at a the distal end of member 110 and out into the space 124 between members 110, 112. This portion of the fluid also eventually exits through port 130. The flow rates through axial and radial passages 120, 122 may be varied through configuration of the passages or other means known in the art. The change in temperature of the fluid flow may be monitored as it passes through space 124 in order to provide an estimate of the energy absorbed by the fluid and, therefore, the energy delivered to tissue 12. ECU 26 may use this information to control delivery of ablation energy through ablation delivery member 108.

Although an exemplary irrigation system has been shown in FIG. 7, it should be understood that a variety of modifications could be made. For example, although the illustrated embodiment shows delivery of irrigating fluid to surfaces near a proximal end of outer member 112, outer member 112 may be modified to define a port at the distal end of member 112 through which irrigation fluid may also, or alternatively, exit member 112 at a distal end of member 112 towards tissue 12. The flow of fluid may also be varied by, for example, installing structures such as dividers or diameter restrictors in various fluid passages to control the flow of fluid by directing fluid flow or by accelerating fluid flow through a given passage (with the benefit of enabling reduced fluid flow). Similarly, valves or other structures may be used to vary the flow rate of the irrigating fluid such as to permit constant flow, intermittent flow, or variable flow. In accordance with one embodiment, a form of pulsative flow (oscillating between relatively higher and lower fluid flow levels at regular or irregular rates) may be used to increase turbulence and thereby prevent stagnation areas around delivery member 108 and to enable periodic and accurate measurement of the temperature of the electrode tip and tissue 12 by the temperature sensors. The flow may be controlled in response to various measured parameters including temperature measured by the temperature sensors or measured impedance (see hereinbelow). A portion of the fluid (e.g., the fluid entering space 124) may be returned through the catheter shaft and exit at a proximal end of the shaft as opposed to exiting through a port in delivery member 108 to the outer surface of member 112. As set forth in U.S. Published Patent Application No. 2010/0152731 titled "Flexible Tip Catheter With Extended Fluid Lumen," the entire disclosure of which is incorporated herein by reference, a porous membrane may extend over a portion or all of the ablation delivery member 58 to permit irrigating fluids to reach tissue 12, but prevent tissue 12 from being pinched in openings in member 58 such as, for example slits 86 in flexible electrodes 76, 78. The membrane may be formed from a material sufficiently conductive to delivery ablation energy to tissue 12. Further information regarding the illustrated irrigation systems and alternative irrigation systems usable with the present invention may be found in commonly assigned and copending U.S. patent application Ser. No. 12/971,645 filed Dec. 17, 2010 and titled "Irrigated Ablation Electrode Assemblies," U.S. patent application Ser. No. 12/979,803 filed Dec. 28, 2010 and titled "Ablation Electrode Assemblies and Methods for Using Same," and U.S. patent application Ser. No. 13/151,750 filed Jun. 2, 2011 and titled "Multi-Rate Fluid Flow and Variable Power Delivery for Ablation Electrode Assemblies Used in Catheter Ablation Procedures," the entire disclosures of which are incorporated herein by reference. As an alternative, or in addition to, use of an irrigation system, catheter 20 may employ vacuum source to draw any blood and fluid entering catheter 20 (e.g. through slits 86 in electrodes 76, 78 of catheter 74) away from the ablation delivery member 58 through shaft 52 and out of body 14 thereby removing fluid closest to member 58 that is the most susceptible to coagulation.

Referring again to FIG. 1, position sensors 60 are provided to indicate the position and orientation of catheter 20 within coordinate system 30 defined by medical position system 16. In the illustrated embodiment, position sensors 60 comprise electrodes. Sensors 60 are placed within body 14 (e.g., within the heart) in electrical fields created by exciting patch electrodes 28. Sensors 60 experience voltages that are dependent on the location between the patch electrodes 28 and the position of the sensors 60 relative to the surface of the heart. Voltage measurement comparisons made between sensors 60 can be used to determine the position of the sensors 60 within body 14. It should also be understood that the type of position sensor used will be dependent on the type of medical position system used. For example, other conventional position sensing systems could be used including magnetic positioning systems such as the system available under the trademark "GMPS" or "MEDI-GUIDE" from St. Jude Medical, Inc. or the system available under the trademark "CARTO" from Biosense Webster, Inc. in which the case the position sensors 60 may comprise magnetic sensors such as coils.

Sensing electrodes 62 may be provided for a variety of diagnostic and therapeutic purposes including, for example, electrophysiological studies, catheter identification and location, pacing, and cardiac mapping and ablation. In the illustrated embodiment, electrodes 62 function as sensing electrodes to sense electrical activity in tissue 12. It should be understood, however, that sensing electrodes 62 could also function as position sensors in a manner similar to position sensors 60. Electrodes 62 may be made from a variety of conductive and biocompatible materials including various metals and metal alloys. Electrodes 62 may comprise ring electrodes. If the orientation of the distal tip of catheter 20 is reasonably discernible, electrodes 62 need not form a complete ring. Instead, button-type electrodes or partial ring electrodes could be used or ring electrodes can be used with an insulative covering selectively removed from portions of the ring. In accordance with one aspect of the invention, sensing electrodes 62 may be closely spaced relative to ablation delivery members 58 and each other. In one embodiment of the invention, the distal edge of one sensing electrode 62 may be disposed about 0.25 millimeters from the proximal edge of an ablation delivery member 58. The distal edge of another sensing electrode 62 may be disposed about 0.5 millimeters from a proximal edge of the one electrode 62. In addition to relatively tight spacing between the electrodes 58, 62, electrodes 62 may be relatively small (e.g. extending for 0.5 mm or 1 mm in the longitudinal direction of the catheter). The relatively close spacing of electrodes 62 relative to one another and relative to ablation delivery member 58 and/or the relatively small size of electrodes 62 enables electrodes 62 to quickly detect attenuation of electric signals in lesions formed by ablation delivery member 58 thereby reducing the amount of ablation energy that must be applied to tissue 12. Electrodes 62 may also have a relatively short length along the longitudinal axis of the catheter. In one embodiment of the invention, electrodes 62 may be about 1.0 millimeters or about 0.5 millimeters. The relatively short length of electrodes further enables quick detection of attenuation of electric signals in lesions formed by ablation delivery member 58.

Figure 8:
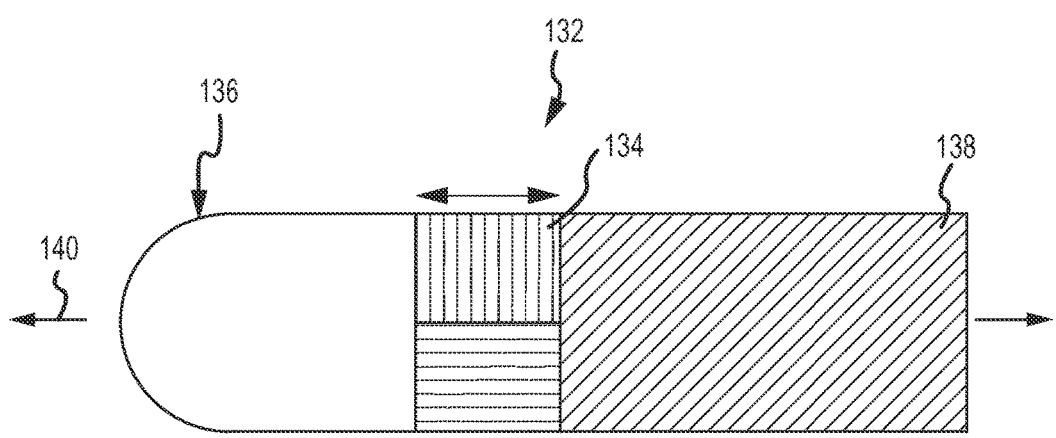
FIG. 8 is a cross-sectional view of another embodiment of an ablation catheter for use in the system of FIG. 1 illustrating one embodiment of a contact sensor.

In accordance with another aspect of the present invention, ablation catheter 20 may further include means for sensing contact between catheter 20 and tissue 12. Referring to FIG. 8, for example, a catheter 132 may include one or more tactile or force contact sensors 134 configured to detect a force applied to an ablation delivery member 136 resulting from contact by member 136 with tissue 12 in order to assess the degree of mechanical coupling between catheter 132 and tissue 12 and, therefore, the delivery of ablation energy to tissue 12. Sensors 134 may generate signals indicative of a change in resistance, voltage, capacitance, impedance or a combination thereof. In the illustrated embodiment, sensors 134 are disposed between the distal end of a shaft 138 of catheter 132 and the ablation delivery member 136. It should be understood, however, that the exact location of sensors 134 may vary provided that they are located so as to sense movement of member 132 in response to contact with tissue 12.

Sensors 134 may comprise, for example, capacitance sensors that generate a signal indicative of a change in capacitance resulting from application of a force. Sensors 134 may also comprise piezoelectric sensors that include a piezoelectric material (in the form of a wire, film or tubes, for example) and generate a signal indicative of a change in voltage resulting from placing the piezoelectric material under stress. Sensors 134 may also comprise pressure sensitive conductive composite (PSCC) sensors (including, but not limited to, quantum tunneling conductive composite (QTC) sensors) in which the electrical resistance of the composite varies inversely in proportion to the pressure that is applied to the composite. Such sensors generate a signal indicative of a change in resistance or conductivity in the composite resulting from application of force. Because the conductivity of PSCC materials changes under stress, PSCC sensors can also be used to selectively transmit ablation energy to ablation delivery member 134 when sufficient contact is achieved (and, in certain embodiments, can themselves comprise the ablation delivery member). Additional information on exemplary sensor embodiments usable with the invention may be found in U.S. Published Patent Application No. 2011/0022045 tilted "Ablation Electrodes With Capacitive Sensors for Resolving Magnitude and Direction of Forces Imparted to a Distal Portion of a Cardiac Catheter," U.S. Published Patent Application No. 2008/0161796 titled "Design of Ablation Electrode With Tactile Sensor," U.S. Published Patent Application No. 2008/0015568 titled "Dynamic Contact Assessment for Electrode Catheters," U.S. Published Patent Application No. 2007/0123764 titled "Systems and Methods for Assessing Tissue Contact," and U.S. Published Patent Application No. 2007/0100332 titled "Systems and Methods for Electrode Contact Assessment," the entire disclosures of which are incorporated herein by reference.

Catheter 132 may include one or more sensors 134 disposed in a plane perpendicular to the longitudinal axis 140 of the catheter 132. Where multiple sensors are used, the sensors may be disposed about the axis 140 with regular or irregular spacing. The use of a multiple sensors 134 enables force detection in a plurality of dimensions including, for example, along the longitudinal axis 140 (stretching and compression) and laterally (bending). The sensor 134 or sensors 134 may be mounted on a support structure within catheter 132 and may be in direct physical contact with ablation delivery member 136 or indirect contact. In particular, an electrical and/or thermal insulator may be disposed between delivery member 136 and any sensor 134.

Sensors 134 generate signals which may be transmitted along conductors connected to sensors 134 and extending through shaft 138 of catheter 132. The signals may be compared to signals generated by a reference electrode coupled to tissue 12 or electrical ground. ECU 26 may use the information generated by sensors 134 to among other things, control the delivery of ablation energy through ablation delivery member 136 by initiating and/or prohibiting delivery of ablation energy when the degree of contact between member 136 and tissue 12 meets or exceeds various predetermined thresholds.

Figure 9:
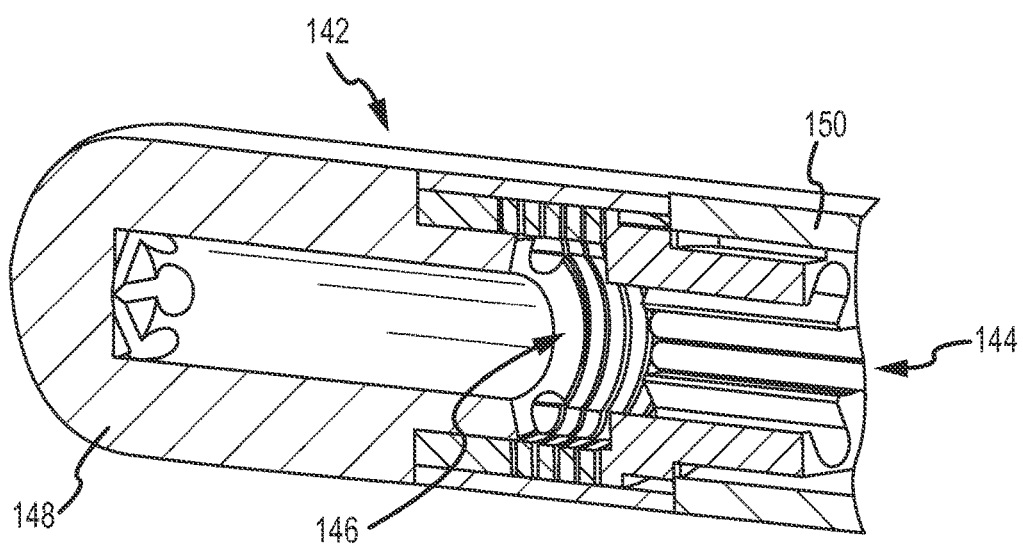
FIG. 9 is a cross-sectional view of another embodiment of an ablation catheter for use in the system of FIG. 1 illustrating another embodiment of a contact sensor.

Referring now to FIG. 9, in another embodiment, a pair of optically interactive elements provides the means for sensing contact between a catheter 142 and tissue 12. In the illustrated embodiment, for example, one or more optical sensors 144 work in combination with an optically interactive surface 146. Sensor 144 may include one or more optic fibers configured to emit and receive light energy from the electromagnetic spectrum. Surface 146 has a known position relative to an ablation delivery member 148 such that a change in position, configuration and/or orientation of surface 146 causes a change in the plane of reflection and a change in a characteristic of light (e.g., intensity, wavelength, phase, spectrum, speed, optical path, interference, transmission, absorption, reflection, refraction, diffraction, polarization and scattering) indicative of a force applied to member 148 by, for example, contact with tissue 12. Surface 146 may be comprised of any material capable of reflecting or refracting light including, for example, polished metals. Refractive media (e.g., a lens or filter) or mediums (air, gel, or liquid including those dispersed or suspended in a solid or solid particulate) may be employed with surface 146. Additional information on exemplary optical sensing assemblies usable with the invention may be found in U.S. Published Patent Application No. 2008/0249522 titled "Irrigated Catheter With Improved Fluid Flow," U.S. Published Patent Application No. 2008/0275428 titled "Optic-Based Contact Sensing Assembly and System," and International (PCT) Published Patent Application No. WO 2010/078453 titled "Optic-Based Contact Sensing Assembly and System," the entire disclosures of which are incorporated herein by reference. Although the illustrated embodiment shows an optical sensor 144 supported within the distal end of a shaft 150 of the catheter 142 and the optically interactive surface 146 supported within ablation delivery member 148, it should be understood that the relative positions of the sensor 144 and surface 146 could be reversed.

In one embodiment, ablation generator 22 generates, delivers and controls RF energy used by ablation catheter 20. Generator 22 is conventional in the art and may comprise the commercially available unit available under the model number IBI-1500T RF Cardiac Ablation Generator, available from St. Jude Medical, Inc. Generator 22 includes an RF ablation signal source 152 configured to generate an ablation signal that is output across a pair of source connectors: a positive polarity connector SOURCE (+) which may connect to ablation delivery member 58; and a negative polarity connector SOURCE(−) which may be electrically connected by conductors or lead wires to an external patch electrode. It should be understood that the term connectors as used herein does not imply a particular type of physical interface mechanism, but is rather broadly contemplated to represent one or more electrical nodes. Source 152 is configured to generate a signal at a predetermined frequency in accordance with one or more user specified parameters (e.g., power, time, etc.) and under the control of various feedback sensing and control circuitry as is know in the art. Source 152 may generate a signal, for example, with a frequency of about 450 kHz or greater. Generator 22 may also monitor various parameters associated with the ablation procedure including impedance, the temperature at the tip of the catheter 20, ablation energy and the position of the catheter 20 and provide feedback to the clinician regarding these parameters.

Display system 24 is provided to convey information to a clinician to assist in diagnosis and treatment. Display system 24 may comprise one or more conventional computer monitors or other display devices. Display system 24 may provide a graphical user interface (GUI) to the clinician. The GUI may include a variety of information including, for example, an image of the geometry of a region of interest in body 14, associated electrophysiology data, graphs illustrating voltage levels over time for various electrodes on catheters 18, 20, and images of catheters 18, 20 and other medical devices and related information indicative of the position of catheters 18, 20 and other devices relative to the region of interest. Examples of the type of information that may be displayed are shown in commonly assigned U.S. Pat. No. 7,263,397 titled "Method and Apparatus for Catheter Navigation and Location and Mapping in the Heart," the entire disclosure of which is incorporated herein by reference.

ECU 26 provides a means for controlling the delivery of ablation energy from ablation delivery member 58. ECU 26 may also be a component of position and navigation system 16 and thereby provide a means for determining the geometry of a region of interest in body 14, electrophysiology characteristics of the region of interest and the position and orientation of catheters 18, 20 relative to the region of interest. ECU 26 also provides a means for generating display signals used to control display system 24. ECU 26 may comprise one or more programmable microprocessors or microcontrollers or may comprise one or more ASICs. ECU 26 may include a central processing unit (CPU) and an input/output (I/O) interface through which ECU 26 may receive a plurality of input signals including signals generated by electrodes on catheters 18, 20 and feedback signals from position and navigation system 16 and generate a plurality of output signals including those used to control and/or provide data to catheters 18, 20 and display system 24. Although a single ECU 26 is shown in the illustrated embodiment for use with catheters 18, 20 and system 16, it should be understood that catheters 18, 20 and system 16 may be configured with individual ECUs.

In accordance with the present teachings, ECU 26 may be configured with programming instructions from a computer program (i.e., software) to implement a method for diagnosis or treatment of tissue 12. In particular, ECU 26 is configured to control the delivery of ablation energy from ablation delivery member 58. ECU 26 controls the delivery of ablation energy at least partly in response to one or more signals indicative of electrical activity in tissue 12 and, in particular, indicative of attenuation of electric signals in lesions formed by ablation delivery member 58. In response to these signals, ECU 26 may evaluate ablative lesions created in tissue 12 by the ablation energy delivered to tissue 12 through ablation delivery member 58 in order to determine the effectiveness of the lesions. Signals indicative of the electrical activity in tissue 12 may be generated by sensing electrodes 62. Alternatively or in addition, ablation delivery member 58 may be used to generate such signals where the ablation delivery member 58 comprises an electrode. In evaluating the lesions, ECU 26 may be further configured to determine a value for a characteristic associated with an intracardiac electrogram. ECU 26 may, for example, determine the amplitude of the electrogram and use that value as an indicator of the attenuation of electrical signals in the lesion. The electrogram may be a unipolar electrogram measured between a return electrode and any of the sensing electrodes 62 or, in certain embodiments, ablation delivery member 58. The electrogram may alternatively comprise a bipolar electrogram measured between any two of the sensing electrodes 62 and, in certain embodiments, ablation delivery member 58, that are spaced longitudinally along the catheter shaft 52

In controlling the delivery of ablation energy to member 58, ECU 26 may further be configured to determine a degree of mechanical and/or electrical coupling between member 58 and tissue 12. ECU 26 may use the degree of coupling in combination with the electrical activity signals referenced hereinabove to control various factors associated with the delivery of ablation energy including the intensity of energy and the time of delivery.

Figure 10:
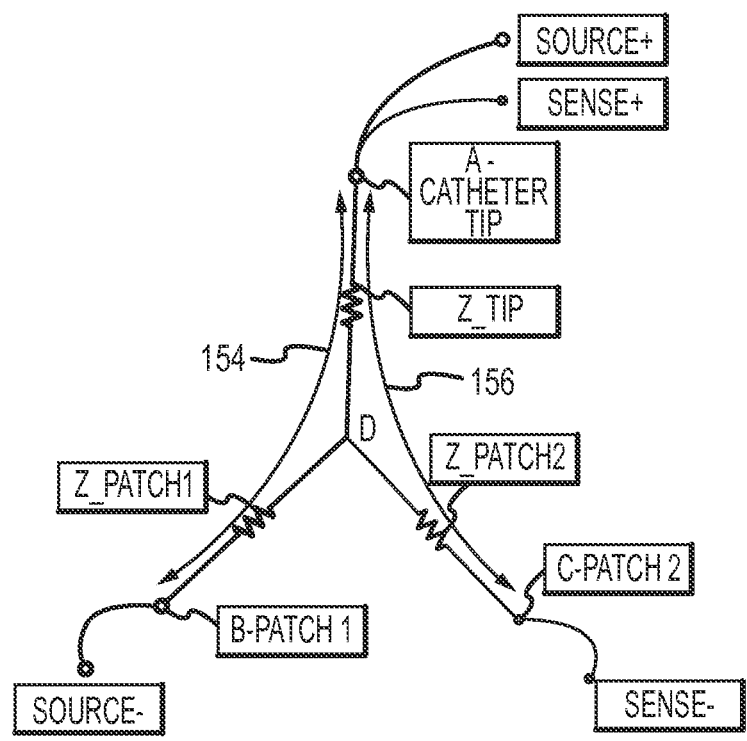
FIG. 10 is a simplified schematic diagram illustrating how impedance at the catheter tissue interface may be determined.

ECU 26 may determine the degree of mechanical coupling responsive to signals indicative of contact forces between catheter 20 and tissue 12 including, for example, signals generated by sensors 134, 144 described hereinabove. ECU 26 may determine the degree of electrical coupling responsive to signals indicative of impedance between ablation delivery member 58 and tissue. As discussed in U.S. Published Patent Application No. 2010/0228247 titled "Assessment of Electrode Coupling of Tissue Ablation," U.S. Published Patent Application No. 2009/0163904 titled "System and Method for Assessing Coupling Between an Electrode and Tissue," and U.S. Published Patent Application No. 2010/0168735 titled "System and Method for Assessing Coupling Between and Electrode and Tissue," the entire disclosures of which are incorporated herein by reference, and with reference to FIG. 10, ECU 26 may enable generation of an excitation signal from a signal source (not shown) across a path 154 from an electrode on catheter 20 (including ablation delivery member 58 where member 58 comprises an electrode) comprising a positive polarity connector SOURCE(+) to a return electrode located, for example, on catheter 20 or body 14 comprising a negative polarity connector SOURCE(−). This signal induces a response signal along a path 156 from the catheter electrode which also comprises a positive polarity connector SENSE(+) to another return electrode on catheter 20 or body 14 comprising a negative polarity connector SENSE(−) that is dependent on the complex impedance at the catheter/tissue interface. Conventional circuits may be used to resolve this signal into component parts for the complex impedance at the catheter/tissue interface allowing ECU 26 to determine values for one or more components of a complex impedance between member 58 and tissue 12. These components may including a resistance between member 58 and tissue 12, a reactance between member 58 and tissue 12, an impedance magnitude between member 58 and tissue 12 and an impedance phase angle between member 58 and tissue 12. ECU 26 may further compute a coupling index responsive to these components and possibly other measurements that is indicative of the degree of coupling and is presented to the clinician on display system 24 or is otherwise made available for use in controlling further delivery of ablation energy.

A system in accordance with the present invention is advantageous because the system enables the clinician to optimize the mechanical and/or electrical coupling of the ablation catheter to the tissue thereby improving the efficacy of the delivery of ablative energy. Further, the inventive system enables the clinician to assess the development of lesions in real time. Each of these improvements may contribute to an optimized application of energy to the tissue during ablation thereby reducing the risks of tissue perforation, steam pops and coagulation of the blood.

Additionally, various medical devices, such as catheters and/or catheter-based systems, may include various combinations of features, structures, and/or characteristics described above and/or disclosed herein to provide additional advantages. For example, in various embodiments and referring specifically to FIGS. 11A-B, a catheter 158 may include an elongate shaft 160, a flexible electrode 162 positioned near a distal end of the shaft 160, and a closely-spaced electrode 164 (FIG. 11A) or 164' (FIG. 11B) positioned proximate the flexible electrode 162. The catheter 158, elongate shaft 160, flexible electrode 162, and closely-spaced electrode 164, 164' may be similar to catheter 20, shaft 52, ablation electrode 76, and sensing electrode 62, described above. The flexible electrode 162 and the closely-spaced electrode 164, 164' may be configured to ablate tissue and/or sense EGM information from tissue, such as that of a heart or other portions of a cardiovascular system (see tissue 12 discussed in relation to FIG. 1, above). The closely-spaced electrode 164, 164' may be positioned a distance D, which may be between about 0.25 mm and about 0.50 mm from the flexible electrode 162. Referring to FIG. 11A, the closely-spaced electrode 164 may comprise a ring electrode, as described above. Alternatively, referring to FIG. 11B, the closely-spaced electrode 164' may comprise a button-type or spot electrode, as described above.

Referring now to FIG. 12, in at least one embodiment, the flexible electrode 162 and/or the closely-spaced electrode 164, 164' may be coupled to an electronic control unit (ECU) 166, similar to ECU 26 described above, configured to compute an electrical coupling index (ECI) indicative of a degree of coupling with tissue which may be presented to a clinician on a display or otherwise made available for use in controlling delivery of ablation energy, as described above. Additionally, the catheter may include one or more force sensing elements, such as force sensing element 168 shown in phantom, coupled to the flexible electrode 162 and/or the closely-spaced electrode 164, 164'. In at least one embodiment, the force sensing element 168 may comprise a mechanical force sensor similar to tactile or force contact sensor 134 described above. Additionally or alternatively, the force sensing element 168 may comprise an optical force sensor similar to optical sensor 144 described above.

Referring still to FIG. 12, the catheter 158 may also include at least one irrigation lumen, defined by irrigation tube 170, for example, configured to deliver an irrigant, such as saline, through, to, and/or near the flexible electrode 162 and/or the closely-spaced electrode 164 or 164'. The irrigation tube 170 may be similar to irrigation tube 104 described above. The flexible electrode 162 may include slits 172 or openings configured to allow irrigant to openly flow through at least a portion of the flexible electrode 162.

Figure 13:
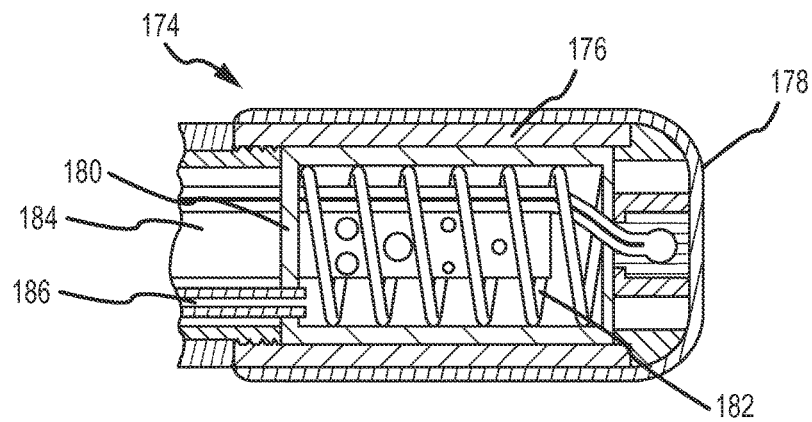
FIG. 13 is a cross-sectional view of another embodiment of an ablation catheter for use in the system of FIG. 1.

Referring now to FIG. 13, in at least one embodiment, a catheter 174, similar to catheter 158 described above, may include a flexible electrode, such as flexible electrode 176 similar to flexible electrode 162 described above. A first membrane 178 may be positioned over at least a portion of the exterior surface of the electrode 176 and/or a second membrane 180 positioned within at least a portion of the electrode 176. A coil 182, similar to coil 102 described above, may provide a support structure for the flexible electrode 176. As illustrated, the second membrane 180 may be coupled to and/or contacting coil 182. In at least one embodiment, one or both membranes 178, 180 may be plugged or otherwise configured such that irrigant, delivered by a lumen defined within irrigation tube 184, is prevented from flowing out of the flexible electrode 176. In such embodiments, the catheter 174 may also include a return lumen defined by return tube 186 configured to return irrigant from the flexible electrode 176. In other words, the catheter 174 may provide a closed-loop irrigation pathway, as irrigant may flow into the flexible electrode 176 through irrigation tube 184 and out of the electrode 176 through the return tube 186. Additionally, one or both membranes 178, 180 may be at least partially porous or plugged such that either or both are configured to allow at least some irrigant to flow therethrough and out of the flexible electrode 176.

Figure 14:
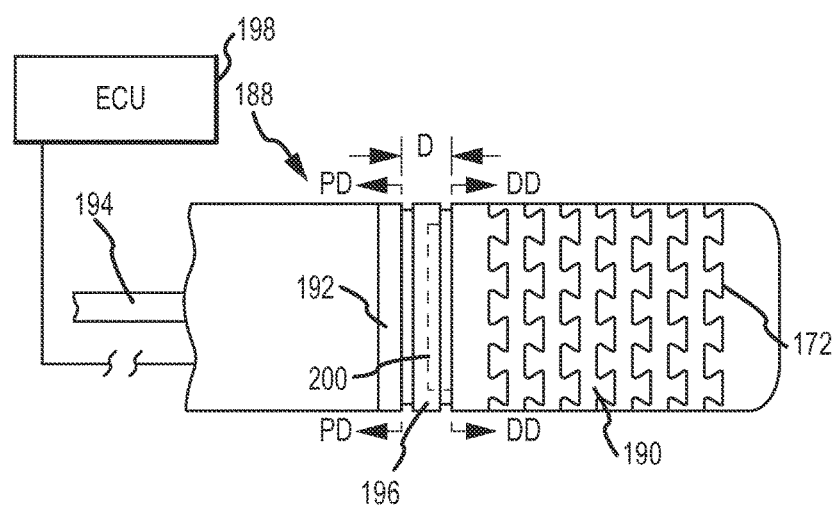
FIG. 14 is a diagrammatic view of another embodiment of an ablation catheter for use in the system of FIG. 1.

Referring now to FIG. 14, in at least one embodiment, a catheter 188, similar to catheter 158, described above, may comprise a flexible electrode 190 and a closely-spaced electrode 192, similar to electrodes 162, 164 (or 164') described above. The catheter 188 may further include an irrigation tube 194, similar to irrigation tube 170 described above, defining an irrigation lumen and an irrigation distribution element 196 disposed near the flexible electrode 190 configured to direct irrigant out of an annular opening or a channel and along a portion of an exterior surface of the flexible electrode 190 in a distal direction, for example (see arrows "DD"). Further, the irrigation distribution element 196 may be a dual or split-flow irrigation element configured to direct irrigant out of a channel and along a portion of an exterior surface of the flexible electrode 190 (in a distal direction DD) and also out of another channel and along a portion of an exterior surface of the closely-spaced electrode 192 in a proximal direction, for example (see arrows "PD"). Additionally, the catheter 188 may be further coupled to an ECU 198, similar to ECU 26 described above, the ECU 198 configured to compute an ECI. Moreover, the catheter 188 may also comprise one or more force sensing elements, such as force sensing element 200 shown in phantom and similar to force sensing element 134 or 144 described above. Although not shown for the purposes of clarity, the catheter 188 may further comprise one or more membranes, similar to membranes 178, 180 described above.

Additionally, while not shown for the purposes of brevity, the features, structures, or characteristics of one or more of catheters 158, 174, and 188 described above may be further combined in various embodiments contemplated herein.

Referring now to FIGS. 15A-B, a catheter 202 may include an elongate shaft 204, a rigid electrode 206 positioned near a distal end of the shaft 204, and a closely-spaced electrode 208 (FIG. 15A) or 208' (FIG. 15B) positioned proximate the rigid electrode 206. The catheter 202, electrode shaft 204, rigid electrode 206 and closely-spaced electrode 208, 208' may be similar to catheter 20, shaft 52, ablation electrode 66, and sensing electrode 62, described above. The rigid electrode 206 and the closely-spaced electrode 208, 208' may be configured to ablate tissue and/or sense EGM information from tissue, such as that of a heart or other portions of a cardiovascular system (see tissue 12 discussed in relation to FIG. 1, above). The closely-spaced electrode 208, 208' may be positioned a distance D, which may be between about 0.25 mm and about 0.50 mm from the rigid electrode 206. Referring to FIG. 15A, the closely-spaced electrode 208 may comprise a ring electrode, as described above. Alternatively, referring to FIG. 15B, the closely-spaced electrode 208' may comprise a button-type or spot electrode, as described above.

Referring now to FIG. 16, in at least one embodiment, the rigid electrode 206 and/or the closely-spaced electrode 208, 208' may be coupled to an electronic control unit (ECU) 210, similar to ECU 26 described above, configured to compute an electrical coupling index (ECI) indicative of a degree of coupling with tissue which may be presented to a clinician on a display or otherwise made available for use in controlling delivery of ablation energy, as described above. Additionally, the catheter may include one or more force sensing elements, such as force sensing element 212 shown in phantom, coupled to the rigid electrode 206 and/or the closely-spaced electrode 208, 208'. In at least one embodiment, the force sensing element 212 may comprise a mechanical force sensor similar to tactile or force contact sensor 134 described above. Additionally or alternatively, the force sensing element 212 may comprise an optical force sensor similar to optical sensor 144 described above.

Referring still to FIG. 16, the catheter 202 may also include at least one irrigation lumen, defined by irrigation tube 214, for example, configured to deliver an irrigant, such as saline, through, to, and/or near the rigid electrode 206 and/or the closely-spaced electrode 208 or 208'. The irrigation tube 214 may be similar to irrigation tube 104 described above. The rigid electrode 206 may include openings configured to allow irrigant to openly flow through at least a portion of the rigid electrode 206.

Figure 17:
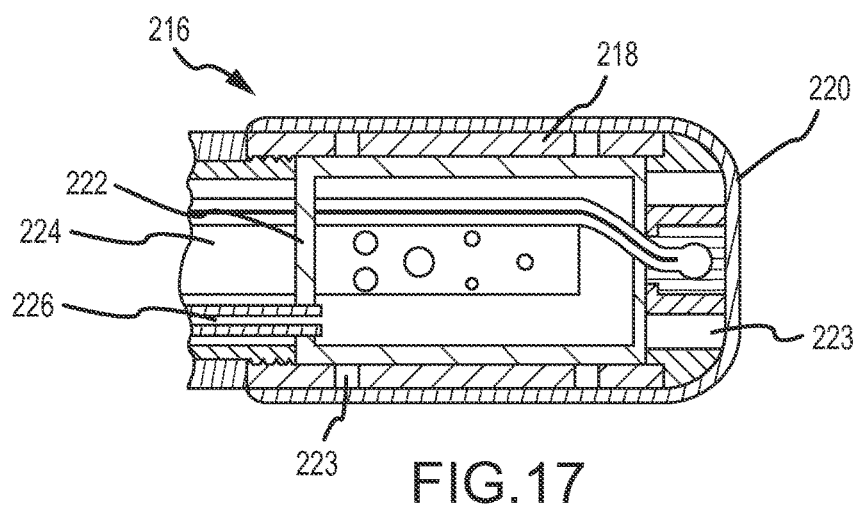
FIG. 17 is a cross-sectional view of another embodiment of an ablation catheter for use in the system of FIG. 1.

Referring now to FIG. 17, in at least one embodiment, a catheter 216, similar to catheter 202 described above, may include a rigid electrode, such as rigid electrode 218 similar to rigid electrode 206 described above. A first membrane 220 may be positioned over at least a portion of the exterior surface of the electrode 206 and/or a second membrane 222 positioned within at least a portion of the electrode 206. In at least one embodiment, one or both membranes 220, 222 may be plugged or otherwise configured such that irrigant, delivered by a lumen defined within irrigation tube 224, is prevented from flowing out of the rigid electrode 218. In such embodiments, the catheter 216 may also include a return lumen defined by return tube 226 configured to return irrigant from the rigid electrode 218. In other words, the catheter 216 may provide a closed-loop irrigation pathway, as irrigant may flow into the rigid electrode 218 through irrigation tube 224 and out of the electrode 218 through the return tube 225. Additionally, one or both membranes 220, 222 may be at least partially porous or plugged such that either or both are configured to allow at least some irrigant to flow therethrough and out of the rigid electrode 218. In such embodiments, irrigant may also pass through ports or openings 223 formed in the electrode 218.

Figure 18:
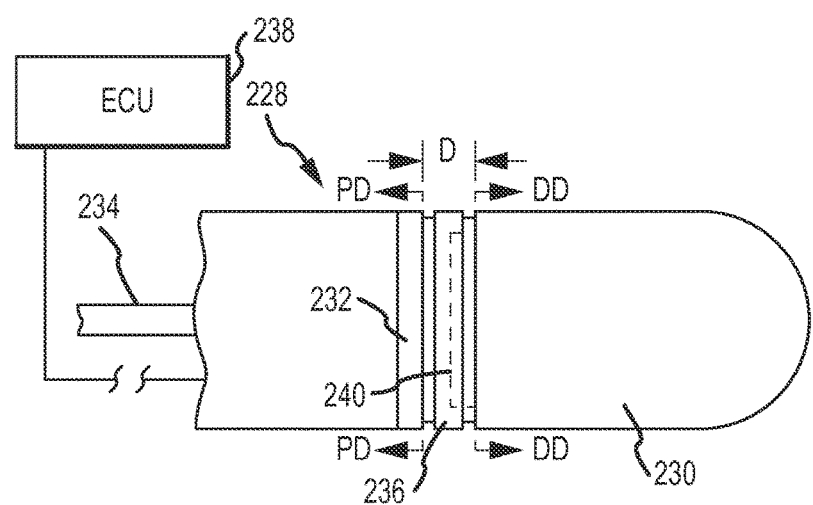
FIG. 18 is a diagrammatic view of another embodiment of an ablation catheter for use in the system of FIG. 1.

Referring now to FIG. 18, in at least one embodiment, a catheter 228, similar to catheter 202, described above, may comprise a rigid electrode 230 and a closely-spaced electrode 232, similar to electrodes 206, 208 (or 208') described above. The catheter 228 may further include an irrigation tube 234, similar to irrigation tube 214 described above, defining an irrigation lumen and an irrigation distribution element 236 disposed near the rigid electrode 230 configured to direct irrigant out of an annular opening or a channel and along a portion of an exterior surface of the rigid electrode 230 in a distal direction, for example (see arrows "DD"). Further, the irrigation distribution element 236 may be a dual or split-flow irrigation element configured to direct irrigant out of a channel and along a portion of an exterior surface of the rigid electrode 230 (in a distal direction DD) and also out of another channel and along a portion of an exterior surface of the closely-spaced electrode 232 in a proximal direction, for example (see arrows "PD"). Additionally, the catheter 228 may be further coupled to an ECU 238, similar to ECU 26 described above, the ECU 238 configured to compute an ECI. Moreover, the catheter 228 may also comprise one or more force sensing elements, such as force sensing element 240 shown in phantom and similar to force sensing element 134 or 144 described above. Although not shown for the purposes of clarity, the catheter 128 may further comprise one or more membranes, similar to membranes 220, 222 described above.

Additionally, while not shown for the purposes of brevity, the features, structures, or characteristics of one or more of catheters 206, 216, and 228 described above may be further combined in various embodiments contemplated herein.

Figure 19A:
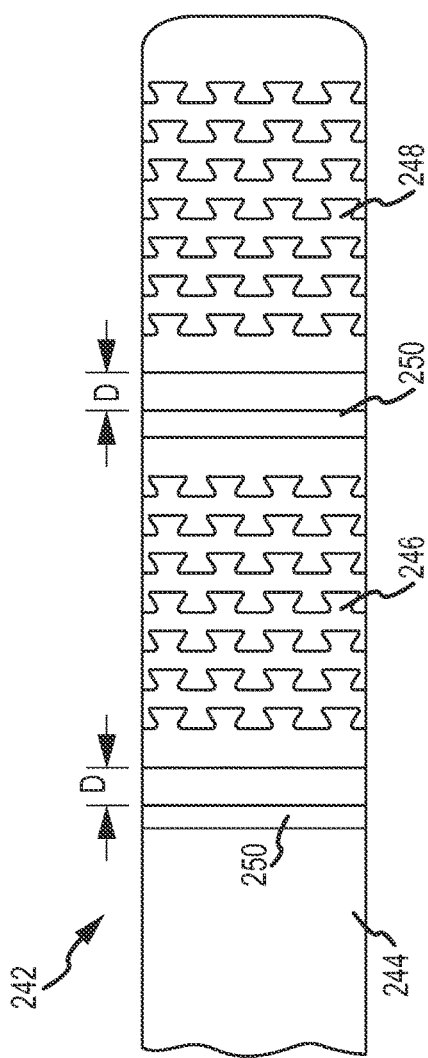
FIGS. 19A-B are plan views of another embodiment of an ablation catheter for use in the system of FIG. 1.
Figure 19B:
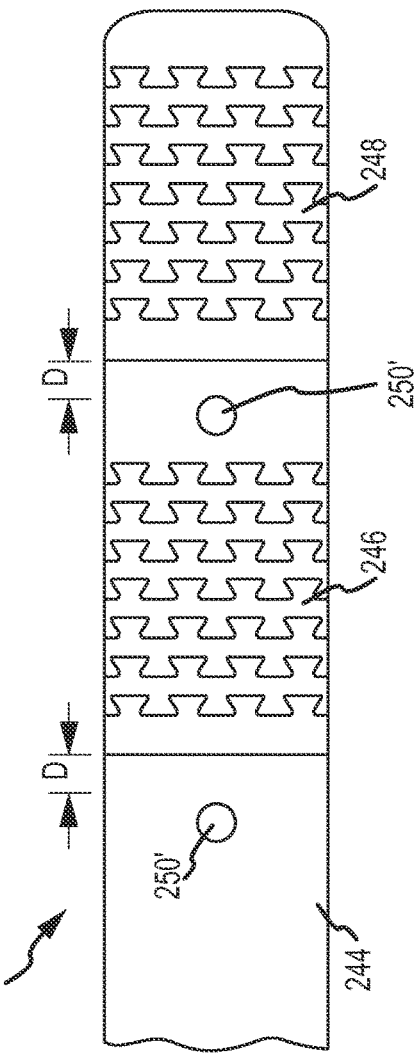

Referring now to FIGS. 19A-B, a catheter 242 may include an elongate shaft 244, a pair of flexible electrodes 246, 248 positioned near a distal end of the shaft 244 and closely-spaced electrodes 250 (FIG. 19A) or 250' (FIG. 19B) positioned proximate one or both of the flexible electrodes 246, 248. The catheter 242, electrode shaft 244, flexible electrodes 246, 248 and closely-spaced electrodes 250, 250' may be similar to catheter 20, shaft 52, flexible electrodes 76, 78, and sensing electrode 62, respectively, described above. The flexible electrodes 246, 248 and the closely-spaced electrodes 250, 250' may be configured to ablate tissue and/or sense EGM information from tissue, such as that of a heart or other portions of a cardiovascular system (see tissue 12 discussed in relation to FIG. 1, above). The closely-spaced electrodes 250, 250' may be positioned a distance D, which may be between about 0.25 mm and about 0.50 mm from one or both of the flexible electrodes 246, 248. Referring to FIG. 19A, the closely-spaced electrode 250 may comprise a ring electrode, as described above. Alternatively, referring to FIG. 19B, the closely-spaced electrode 250' may comprise a button-type or spot electrode, as described above.

Figure 20:
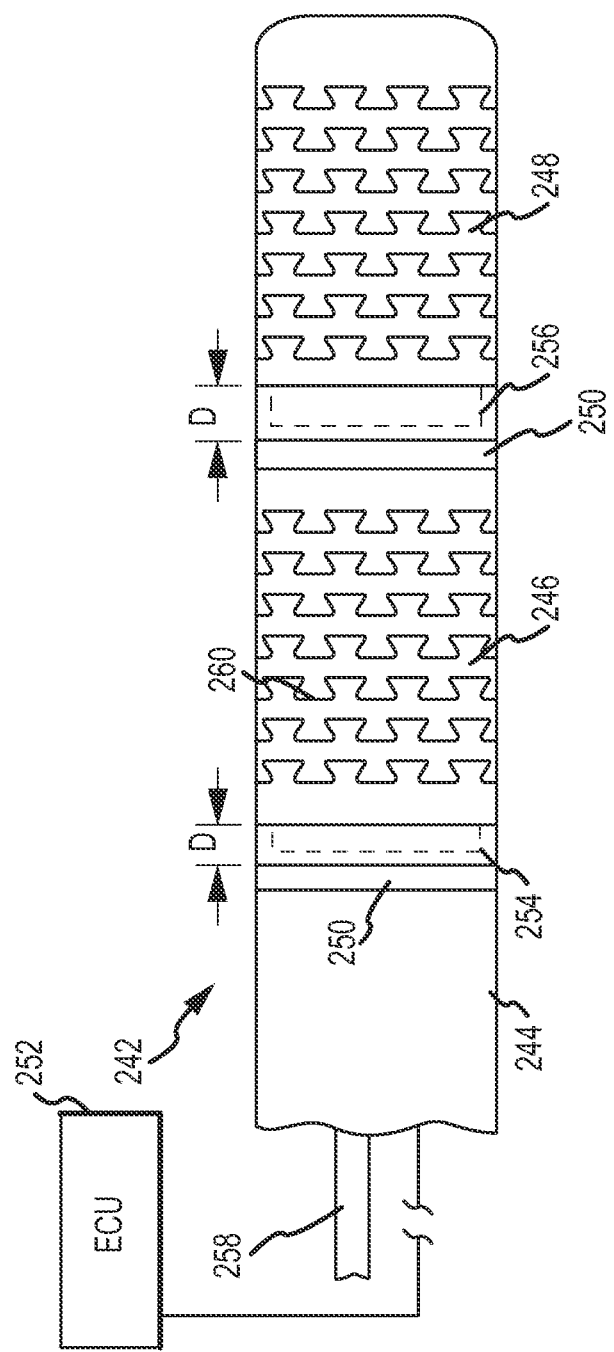
FIG. 20 is a diagrammatic view of another embodiment of the catheter of FIGS. 19A-B.

Referring now to FIG. 20, in at least one embodiment, the flexible electrodes 246, 248 and/or the closely-spaced electrode 250, 250' may be coupled to an electronic control unit (ECU) 252, similar to ECU 26 described above, configured to compute an electrical coupling index (ECI) indicative of a degree of coupling with tissue which may be presented to a clinician on a display or otherwise made available for use in controlling delivery of ablation energy, as described above. Additionally, the catheter may include one or more force sensing elements, such as force sensing element 254, 256 shown in phantom, coupled to the flexible electrodes 246, 248 and/or the closely-spaced electrode 250, 250'. In at least one embodiment, the force sensing elements 254, 256 may comprise a mechanical force sensor similar to tactile or force contact sensor 134 described above. Additionally or alternatively, the force sensing elements 254, 256 may comprise an optical force sensor similar to optical sensor 144 described above.

Referring still to FIG. 20, the catheter 242 may also include at least one irrigation lumen, defined by irrigation tube 258, for example, configured to deliver an irrigant, such as saline, through, to, and/or near the one or both of flexible electrodes 246, 248 and/or the closely-spaced electrode 250 or 250'. The irrigation tube 258 may be similar to irrigation tube 104 described above. The flexible electrodes 246, 248 may include openings (such as slits 260) configured to allow irrigant to openly flow through at least a portion of the electrodes 246, 248.

Figure 21:
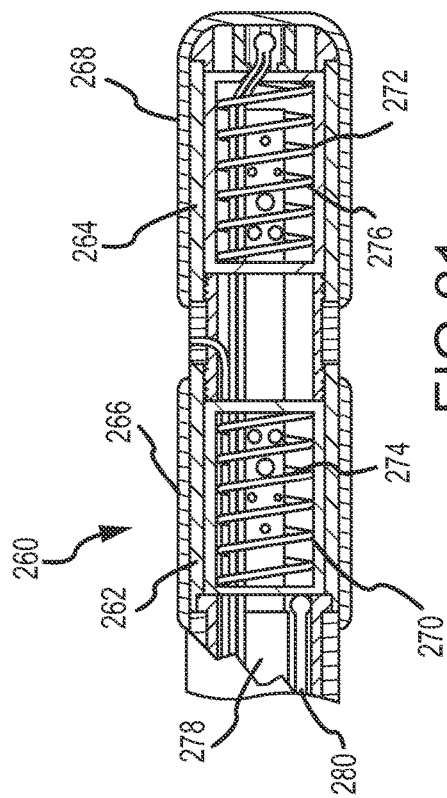
FIG. 21 is a cross-sectional view of another embodiment of an ablation catheter for use in the system of FIG. 1.

Referring now to FIG. 21, in at least one embodiment, a catheter 260, similar to catheter 242 described above, may include flexible electrodes 262, 264 similar to flexible electrodes 246, 248 described above. First membranes 266, 268 may be positioned over at least a portion of the exterior surface of one or both electrodes 262, 264 and/or second membranes 270, 272 positioned within at least a portion of one or both electrodes 262, 264. Coils 274, 276, similar to coil 102 described above, may provide a support structure for the electrode 262, 264. As illustrated, the second membrane 270 and/or 272 may be coupled to and/or contacting a corresponding coil 274, 276. In at least one embodiment, one or more of membranes 266, 268, 270, 272 may be plugged or otherwise configured such that irrigant, delivered by a lumen defined within irrigation tube 278, is prevented from flowing out of a corresponding electrode 262, 264. In such embodiments, the catheter 260 may also include a return lumen defined by return tube 280 configured to return irrigant from the electrodes 262, 264. In other words, the catheter 260 may provide a closed-loop irrigation pathway, as irrigant may flow into the electrodes 262, 264 through irrigation tube 278 and out of the electrodes 262, 264 through the return tube 280. Additionally, one or more of membranes 266, 268, 270, 272 may be at least partially porous or plugged such that either or both are configured to allow at least some irrigant to flow therethrough and out of one or both electrodes 262, 264.

Figure 22:
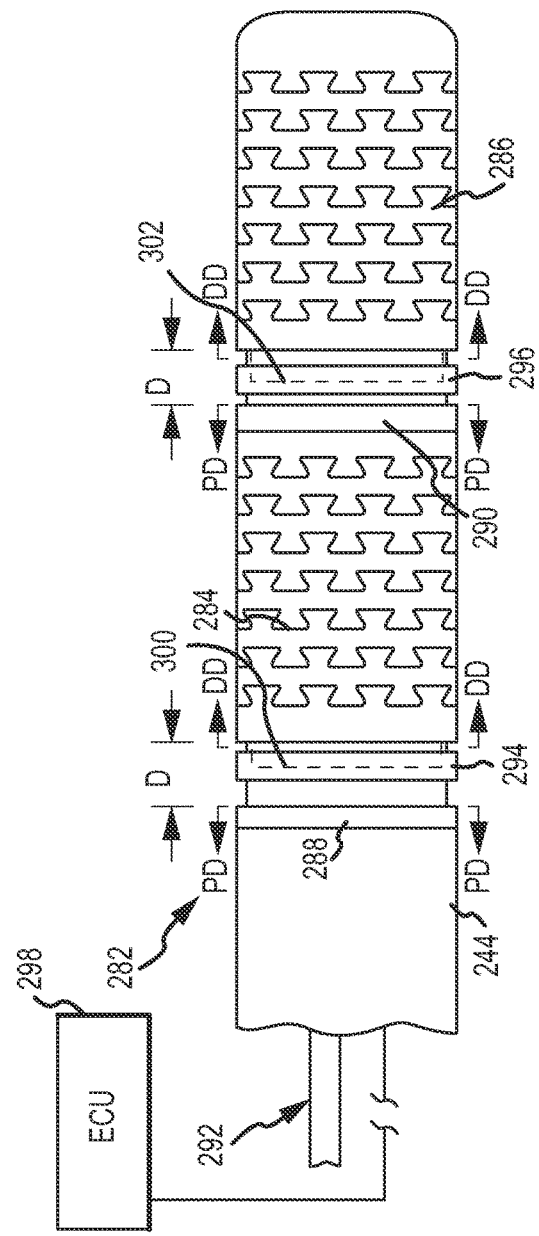
FIG. 22 is a diagrammatic view of another embodiment of an ablation catheter for use in the system of FIG. 1.

Referring now to FIG. 22, in at least one embodiment, a catheter 282, similar to catheter 242, described above, may include flexible electrodes 284, 286 and closely-spaced electrodes 288, 290, similar to electrodes 250 (or 250') described above. The catheter 282 may further include an irrigation tube 292, similar to irrigation tube 258 described above, defining an irrigation lumen and irrigation distribution element 294, 296 disposed near the flexible electrodes 284, 286 configured to direct irrigant out of a channel and along a portion of an exterior surface of the electrodes 284, 286 in a distal direction, for example (see arrows "DD"). Further, the irrigation distribution elements 294, 296 may be dual or split-flow irrigation element configured to direct irrigant out of an annular opening or a channel and along a portion of an exterior surface of the electrodes 294, 296 (in a distal direction DD) and also out of another channel and along a portion of an exterior surface of the closely-spaced electrodes 288, 290 in a proximal direction, for example (see arrows "PD"). Additionally, the catheter 282 may be further coupled to an ECU 298, similar to ECU 26 described above, the ECU 298 configured to compute an ECI. Moreover, the catheter 282 may also comprise one or more force sensing elements, such as force sensing elements, 300, 302 shown in phantom and similar to force sensing element 134 or 144 described above. Although not shown for the purposes of clarity, the catheter 282 may further comprise one or more membranes, similar to membranes 266, 268, 270, 272 described above.

Additionally, while not shown for the purposes of brevity, the features, structures, or characteristics of one or more of catheters 242, 260, 282 described above may be further combined in various embodiments contemplated herein.

Referring now to FIGS. 23A-B, a catheter 304 may include an elongate shaft 306, a flexible electrode 308 and a rigid electrode 310 positioned near a distal end of the shaft 306 with the flexible electrode 308 located proximal the rigid electrode 310 (and the rigid electrode 310 located distal to the flexible electrode 308). Catheter 304 may further include closely-spaced electrodes 312 (FIG. 23A) or 312' (FIG. 23B) positioned proximate one or both of the flexible and rigid electrodes 308, 310. The catheter 304, electrode shaft 306, flexible electrode 308, rigid electrode 310 and closely-spaced electrodes 312, 312' may be similar to catheter 20, shaft 52, flexible electrode 78, ablation electrode 66, and sensing electrode 62, respectively, described above. The flexible electrode 308, rigid electrode 310 and the closely-spaced electrodes 312, 312' may be configured to ablate tissue and/or sense EGM information from tissue, such as that of a heart or other portions of a cardiovascular system (see tissue 12 discussed in relation to FIG. 1, above). The closely-spaced electrodes 312, 312' may be positioned a distance D, which may be between about 0.25 mm and about 0.50 mm from one or both of the flexible electrode 308 and the rigid electrode 310. Referring to FIG. 23A, the closely-spaced electrode 312 may comprise a ring electrode, as described above. Alternatively, referring to FIG. 19B, the closely-spaced electrode 312' may comprise a button-type or spot electrode, as described above.

Figure 24:
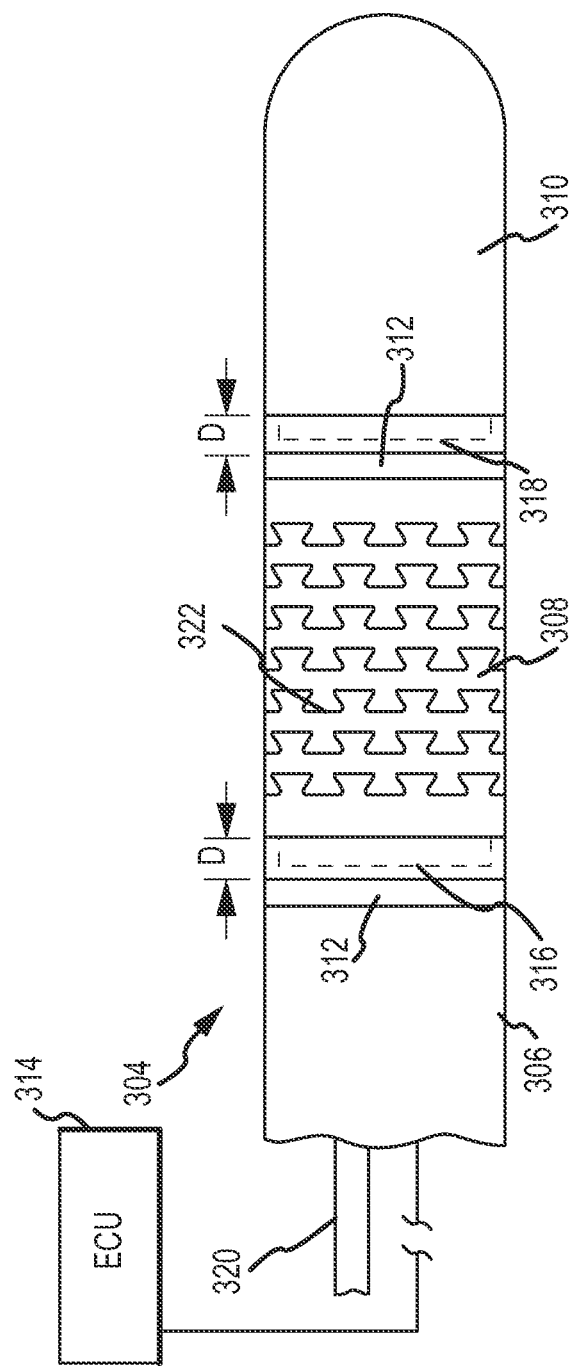
FIG. 24 is a diagrammatic view of another embodiment of the catheter of FIGS. 23A-B.

Referring now to FIG. 24, in at least one embodiment, the flexible electrode 308, rigid electrode 310 and/or the closely-spaced electrode 312, 312' may be coupled to an electronic control unit (ECU) 314, similar to ECU 26 described above, configured to compute an electrical coupling index (ECI) indicative of a degree of coupling with tissue which may be presented to a clinician on a display or otherwise made available for use in controlling delivery of ablation energy, as described above. Additionally, the catheter may include one or more force sensing elements, such as force sensing element 316, 318 shown in phantom, coupled to the flexible electrode 308, rigid electrode 310 and/or the closely-spaced electrode 312, 312'. In at least one embodiment, the force sensing elements 316, 318 may comprise a mechanical force sensor similar to tactile or force contact sensor 134 described above. Additionally or alternatively, the force sensing elements 316, 318 may comprise an optical force sensor similar to optical sensor 144 described above.

Referring still to FIG. 24, the catheter 304 may also include at least one irrigation lumen, defined by irrigation tube 320, for example, configured to deliver an irrigant, such as saline, through, to, and/or near the one or both of flexible electrode 308 and rigid electrode 310 and/or the closely-spaced electrode 312 or 312'. The irrigation tube 320 may be similar to irrigation tube 104 described above. The flexible electrode 308 and the rigid electrode 310 may include openings (such as slits 322 in flexible electrode 308) configured to allow irrigant to openly flow through at least a portion of the electrodes 308, 310.

Figure 25:
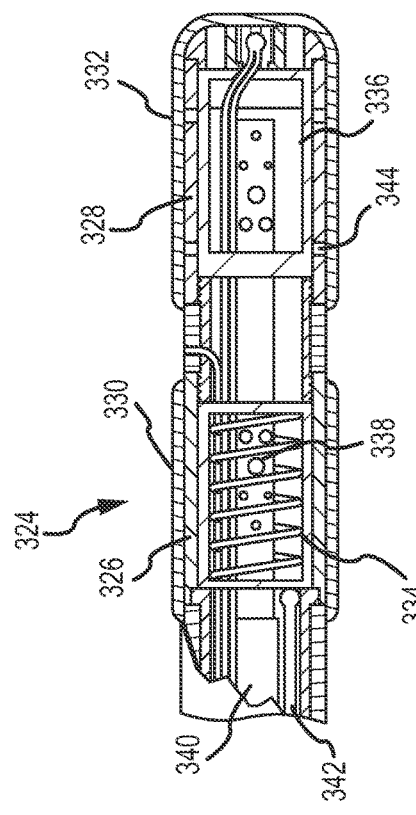
FIG. 25 is a cross-sectional view of another embodiment of an ablation catheter for use in the system of FIG. 1.

Referring now to FIG. 25, in at least one embodiment, a catheter 324, similar to catheter 304 described above, may include a flexible electrode 326 and rigid electrode 328 similar to flexible electrode 308 and rigid electrode 310 described above. First membranes 330, 332 may be positioned over at least a portion of the exterior surface of one or both electrodes 326, 328 and/or second membranes 334, 336 positioned within at least a portion of one or both electrodes 326, 328. A coils 338, similar to coil 102 described above, may provide a support structure for the electrode 326. As illustrated, the second membrane 334 may be coupled to and/or contact coil 338. In at least one embodiment, one or more of membranes 330, 332, 334, 336 may be plugged or otherwise configured such that irrigant, delivered by a lumen defined within irrigation tube 340, is prevented from flowing out of a corresponding electrode 326, 328. In such embodiments, the catheter 324 may also include a return lumen defined by return tube 342 configured to return irrigant from the electrodes 326, 328. In other words, the catheter 324 may provide a closed-loop irrigation pathway, as irrigant may flow into the electrodes 326, 328 through irrigation tube 340 and out of the electrodes 326, 328 through the return tube 342. Additionally, one or more of membranes 330, 332, 334, 336 may be at least partially porous or plugged such that either or both are configured to allow at least some irrigant to flow therethrough and out of one or both electrodes 326, 328. In such embodiments, irrigant may also pass through ports or openings 344 formed in the electrode 328.

Figure 26:
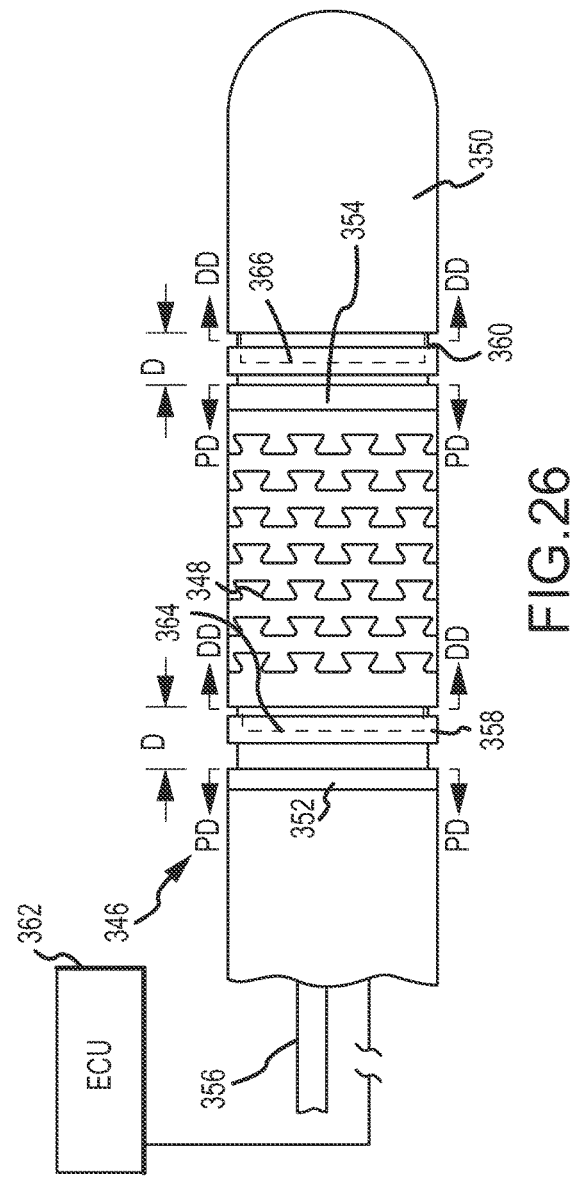
FIG. 26 is a diagrammatic view of another embodiment of an ablation catheter for use in the system of FIG. 1.

Referring now to FIG. 26, in at least one embodiment, a catheter 346, similar to catheter 304, described above, may include flexible and rigid electrodes 348, 350 and closely-spaced electrodes 352, 354, similar to electrodes 312 (or 312') described above. The catheter 346 may further include an irrigation tube 356, similar to irrigation tube 320 described above, defining an irrigation lumen and irrigation distribution element 358, 360 disposed near the flexible and rigid electrodes 348, 350 configured to direct irrigant out of an annular opening or a channel and along a portion of an exterior surface of the electrodes 348, 350 in a distal direction, for example (see arrows "DD"). Further, the irrigation distribution elements 358, 360 may be dual or split-flow irrigation element configured to direct irrigant out of a channel and along a portion of an exterior surface of the electrodes 348, 350 (in a distal direction DD) and also out of another channel and along a portion of an exterior surface of the closely-spaced electrodes 352, 354 in a proximal direction, for example (see arrows "PD"). Additionally, the catheter 346 may be further coupled to an ECU 362, similar to ECU 26 described above, the ECU 362 configured to compute an ECI. Moreover, the catheter 346 may also comprise one or more force sensing elements, such as force sensing elements, 364, 366 shown in phantom and similar to force sensing element 134 or 144 described above. Although not shown for the purposes of clarity, the catheter 346 may further comprise one or more membranes, similar to membranes 330, 332, 334, 336 described above.

Additionally, while not shown for the purposes of brevity, the features, structures, or characteristics of one or more of catheters 304, 324, 346 described above may be further combined in various embodiments contemplated herein.

Referring now to FIGS. 27A-B, a catheter 368 may include an elongate shaft 370, a rigid electrode 372 and a flexible electrode 374 positioned near a distal end of the shaft 370 with the rigid electrode 372 located proximal the flexible electrode 374 (and the flexible electrode 374 located distal to the rigid electrode 372). Catheter 368 may further include closely-spaced electrodes 376 (FIG. 27A) or 376' (FIG. 27B) positioned proximate one or both of the rigid and flexible electrodes 372, 374. The catheter 368, electrode shaft 370, rigid electrode 372, flexible electrode 374 and closely-spaced electrodes 376, 376' may be similar to catheter 20, shaft 52, electrode 66, flexible electrode 76, and sensing electrode 62, respectively, described above. The rigid electrode 372, flexible electrode 374 and the closely-spaced electrodes 376, 376' may be configured to ablate tissue and/or sense EGM information from tissue, such as that of a heart or other portions of a cardiovascular system (see tissue 12 discussed in relation to FIG. 1, above). The closely-spaced electrodes 376, 376' may be positioned a distance D, which may be between about 0.25 mm and about 0.50 mm from one or both of the rigid electrode 372 and the flexible electrode 374. Referring to FIG. 27A, the closely-spaced electrode 376 may comprise a ring electrode, as described above. Alternatively, referring to FIG. 27B, the closely-spaced electrode 376' may comprise a button-type or spot electrode, as described above.

Figure 28:
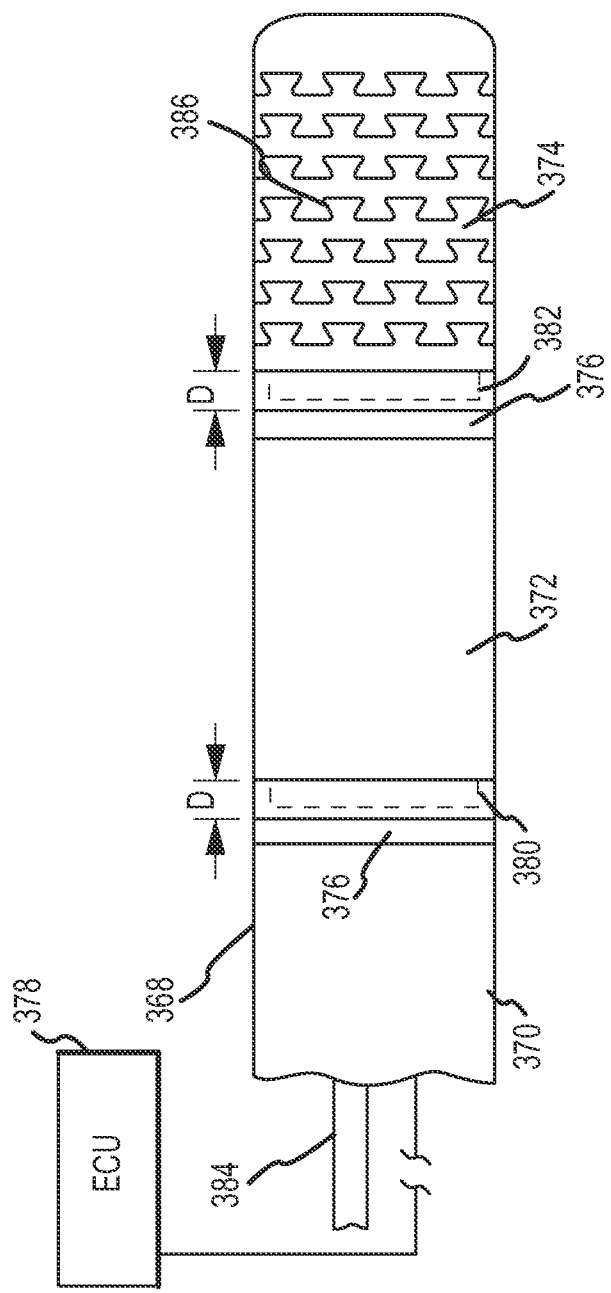
FIG. 28 is a diagrammatic view of another embodiment of the catheter of FIGS. 27A-B.

Referring now to FIG. 28, in at least one embodiment, the rigid electrode 372, flexible electrode 374 and/or the closely-spaced electrodes 376, 376' may be coupled to an electronic control unit (ECU) 378, similar to ECU 26 described above, configured to compute an electrical coupling index (ECI) indicative of a degree of coupling with tissue which may be presented to a clinician on a display or otherwise made available for use in controlling delivery of ablation energy, as described above. Additionally, the catheter may include one or more force sensing elements, such as force sensing element 380, 382 shown in phantom, coupled to the rigid electrode 372, flexible electrode 374 and/or the closely-spaced electrodes 376, 376'. In at least one embodiment, the force sensing elements 380, 382 may comprise a mechanical force sensor similar to tactile or force contact sensor 134 described above. Additionally or alternatively, the force sensing elements 380, 382 may comprise an optical force sensor similar to optical sensor 144 described above.

Referring still to FIG. 28, the catheter 368 may also include at least one irrigation lumen, defined by irrigation tube 384, for example, configured to deliver an irrigant, such as saline, through, to, and/or near the one or both of rigid electrode 372 and flexible electrode 374 and/or the closely-spaced electrodes 376 or 376'. The irrigation tube 384 may be similar to irrigation tube 104 described above. The rigid electrode 372 and the flexible electrode 374 may include openings (such as slits 386 in flexible electrode 374) configured to allow irrigant to openly flow through at least a portion of the electrodes 372, 374.

Figure 29:
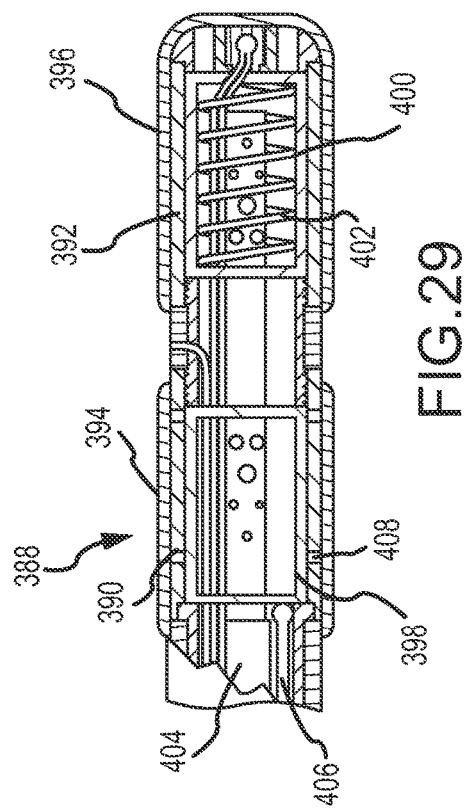
FIG. 29 is a cross-sectional view of another embodiment of an ablation catheter for use in the system of FIG. 1.

Referring now to FIG. 29, in at least one embodiment, a catheter 388, similar to catheter 368 described above, may include a rigid electrode 390 and flexible electrode 392 similar to rigid electrode 372 and flexible electrode 374 described above. First membranes 394, 396 may be positioned over at least a portion of the exterior surface of one or both electrodes 390, 392 and/or second membranes 398, 400 positioned within at least a portion of one or both electrode 390, 392. A coil 402, similar to coil 102 described above, may provide a support structure for the electrode 390, 392. As illustrated, the second membrane 400 may be coupled to and/or contact a coil 402. In at least one embodiment, one or more of membranes 394, 396, 398, 400 may be plugged or otherwise configured such that irrigant, delivered by a lumen defined within irrigation tube 404, is prevented from flowing out of a corresponding electrode 390, 392. In such embodiments, the catheter 388 may also include a return lumen defined by return tube 406 configured to return irrigant from the electrodes 390, 392. In other words, the catheter 388 may provide a closed-loop irrigation pathway, as irrigant may flow into the electrodes 390, 392 through irrigation tube 404 and out of the electrodes 390, 392 through the return tube 406. Additionally, one or more of membranes 394, 396, 398, 400 may be at least partially porous or plugged such that either or both are configured to allow at least some irrigant to flow therethrough and out of one or both electrodes 390, 392. In such embodiments, irrigant may also pass through ports or openings 408 formed in the electrode 390.

Figure 30:
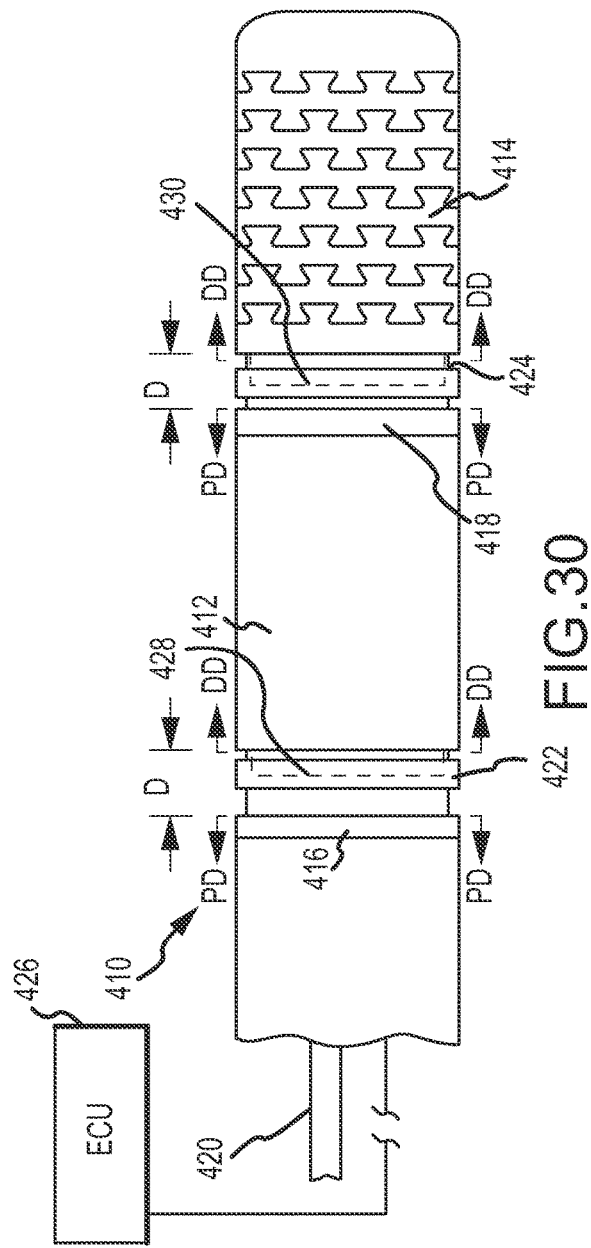
FIG. 30 is a diagrammatic view of another embodiment of an ablation catheter for use in the system of FIG. 1.

Referring now to FIG. 30, in at least one embodiment, a catheter 410, similar to catheter 368, described above, may include rigid and flexible electrodes 412, 414 and closely-spaced electrodes 416, 418 similar to electrodes 376 (or 376') described above. The catheter 410 may further include an irrigation tube 420, similar to irrigation tube 384 described above, defining an irrigation lumen and irrigation distribution element 422, 424 disposed near the rigid and flexible electrodes 412, 414 configured to direct irrigant out of an annular opening or a channel and along a portion of an exterior surface of the electrodes 412, 414 in a distal direction, for example (see arrows "DD"). Further, the irrigation distribution elements 422, 424 may be dual or split-flow irrigation element configured to direct irrigant out of a channel and along a portion of an exterior surface of the electrodes 412, 414 (in a distal direction DD) and also out of another channel and along a portion of an exterior surface of the closely-spaced electrodes 412, 414 in a proximal direction, for example (see arrows "PD"). Additionally, the catheter 410 may be further coupled to an ECU 426, similar to ECU 26 described above, the ECU 426 configured to compute an ECI. Moreover, the catheter 368 may also comprise one or more force sensing elements, such as force sensing elements, 428, 430 shown in phantom and similar to force sensing element 134 or 144 described above. Although not shown for the purposes of clarity, the catheter 410 may further comprise one or more membranes, similar to membranes 394, 396, 398, 400 described above.

Additionally, while not shown for the purposes of brevity, the features, structures, or characteristics of one or more of catheters 368, 388, 410 described above may be further combined in various embodiments contemplated herein.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims. Reference herein to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for diagnosis or treatment of tissue in a body, comprising:
   an ablation catheter, comprising:
   a deformable, elongate shaft having proximal and distal ends;
   a first ablation delivery member disposed proximate said distal end of said deformable, elongate shaft, said first ablation delivery member configured to deliver ablation energy to ablate said tissue, said first ablation delivery member disposed about a longitudinal axis of said deformable, elongate shaft and having proximal and distal ends, said first ablation delivery member including at least one elongate slit configured to permit movement of the ablation delivery member laterally and axially from a first position to a second position relative to said longitudinal axis between said proximal and distal ends of said first ablation delivery member;

a lumen located within the ablation delivery member, the lumen adapted to deliver fluid configured to control the temperature of the first ablation delivery member;

a return lumen configured to draw the fluid away from the first ablation delivery member;

a membrane positioned over at least a portion of the at least one elongate slit and an exterior surface of the ablation delivery member, the membrane configured to prevent the fluid from flowing out of the ablation delivery member to provide a closed-loop pathway between the lumen and the return lumen;

a first sensing electrode disposed proximate said first ablation delivery member, said first sensing electrode configured to generate a first signal indicative of electrical activity in said tissue;

a force sensor disposed proximate the first ablation delivery member, said force sensor configured to generate a second signal; and an electronic control unit configured to control delivery of said ablation energy from said first ablation delivery member responsive to said first signal and to determine a degree of coupling between said first ablation delivery member and said tissue from the first signal and determine a contact force responsive to said second signal, wherein the degree of coupling comprises determining a value for at least one component of a complex impedance between said first ablation delivery member and said tissue, and wherein the electronic control unit is further configured to use the first signal and the second signal to adjust the application of energy to the first ablation delivery member.

2. The system of claim 1 further comprising a second ablation delivery member spaced longitudinally along said deformable, elongate shaft from said first ablation delivery member, said second ablation delivery member configured to deliver said ablation energy to ablate said tissue.

3. The system of claim 2, wherein said first sensing electrode is disposed between said first and second ablation delivery members along said deformable, elongate shaft.

4. The system of claim 1 further comprising a second sensing electrode spaced longitudinally along said deformable, elongate shaft from said first sensing electrode, said second sensing electrode configured to generate a second signal indicative of said electrical activity in said tissue.

5. The system of claim 1, wherein said first ablation delivery member comprises an ablation electrode and said ablation energy comprises radio frequency ablation energy.

6. The system of claim 5, wherein said ablation electrode is configured to generate a second signal indicative of said electrical activity in said tissue.

7. The system of claim 1, wherein said first ablation delivery member includes a sidewall having a plurality of elongated slits extending therethrough.

8. The system of claim 1, wherein said at least one component of said complex impedance comprises one of a resistance between said first ablation delivery member and said tissue and a reactance between said first ablation delivery member and said tissue.

9. The system of claim 1, wherein said at least one component of said complex impedance comprises one of an impedance magnitude between said first ablation delivery element and said tissue and an impedance phase angle between said first ablation delivery member and said tissue.

10. The system of claim 1, wherein said electronic control unit is further configured, in controlling delivery of said ablation energy, to evaluate an ablative lesion created in said tissue by said ablation energy.

11. The system of claim 10, wherein said electronic control unit is further configured, in evaluating said ablative lesion, to determine a value for a characteristic associated with an intracardiac electrogram.

12. The system of claim 11, wherein said intracardiac electrogram comprises a unipolar electrogram measured between said first sensing electrode and a return electrode.

13. The system of claim 11, wherein said intracardiac electrogram comprises a bipolar electrogram measured between said first sensing electrode and a second sensing electrode spaced longitudinally along said deformable, elongate shaft from said first sensing electrode, said second sensing electrode configured to generate a second signal indicative of said electrical activity in said tissue.

14. The system of claim 1, wherein a distal edge of said first sensing electrode is disposed less than or equal to 0.5 mm from a proximal edge of said first ablation delivery member.

15. The system of claim 1 further comprising a position sensor disposed proximate said distal end of said deformable, elongate shaft, wherein said electronic control unit is configured to determine a position of said deformable, elongate shaft within a coordinate system responsive to a position signal generated by said position sensor.

16. The system of claim 1 further comprising a second membrane positioned within at least a portion of the first ablation delivery member.

17. The system of claim 1, wherein the electronic control unit is further configured to monitor the temperature of the fluid within the ablation delivery member to estimate the energy absorbed by the fluid, and wherein the electronic control unit is configured to control delivery of ablation energy based on the estimated energy absorbed.

* * * * *